(12) United States Patent
Berenson

(10) Patent No.: US 11,635,435 B2
(45) Date of Patent: Apr. 25, 2023

(54) DIAGNOSTIC, PROGNOSTIC, AND MONITORING METHODS FOR SOLID TUMOR CANCERS

(71) Applicant: OncoTracker, Inc., West Hollywood, CA (US)

(72) Inventor: James Richard Berenson, Beverly Hills, CA (US)

(73) Assignee: ONCOTRACKER, INC., West Hollywood, CA (US)

( * ) Notice: Subject to any disclaimer, the term of this patent is extended or adjusted under 35 U.S.C. 154(b) by 211 days.

(21) Appl. No.: 16/621,197

(22) PCT Filed: Jun. 13, 2018

(86) PCT No.: PCT/US2018/037275
§ 371 (c)(1),
(2) Date: Dec. 10, 2019

(87) PCT Pub. No.: WO2018/231944
PCT Pub. Date: Dec. 20, 2018

(65) Prior Publication Data
US 2020/0264184 A1  Aug. 20, 2020

Related U.S. Application Data

(60) Provisional application No. 62/518,734, filed on Jun. 13, 2017.

(51) Int. Cl.
*G01N 33/574* (2006.01)

(52) U.S. Cl.
CPC . *G01N 33/57488* (2013.01); *G01N 33/57415* (2013.01); *G01N 2333/525* (2013.01)

(58) Field of Classification Search
CPC ....... G01N 33/57488; G01N 33/57415; G01N 2333/525
See application file for complete search history.

(56) References Cited

U.S. PATENT DOCUMENTS

| | | | |
|---|---|---|---|
| 4,493,795 A | 1/1985 | Nestor, Jr. et al. |
| 4,816,567 A | 3/1989 | Cabilly et al. |
| 5,712,291 A | 1/1998 | D'amato |
| 6,258,540 B1 | 7/2001 | Lo et al. |
| 6,355,623 B2 | 3/2002 | Seidman et al. |
| 7,598,257 B2 | 10/2009 | Rodgers et al. |
| 10,126,301 B2 | 11/2018 | Berenson et al. |
| 2006/0084055 A1 | 4/2006 | Gaiger et al. |
| 2006/0136136 A1 | 6/2006 | Karpusas |
| 2007/0207474 A1 | 9/2007 | Ansell et al. |
| 2007/0212733 A1 | 9/2007 | Martin |
| 2008/0050381 A1 | 2/2008 | Takeuchi et al. |
| 2008/0058316 A1 | 3/2008 | Eberhart et al. |
| 2008/0268480 A1 | 10/2008 | Hsu et al. |
| 2008/0312259 A1 | 12/2008 | Rodgers et al. |
| 2009/0191203 A1 | 7/2009 | Belloir et al. |
| 2010/0285020 A1 | 11/2010 | Aifantis et al. |
| 2013/0101599 A1 | 4/2013 | Borges et al. |
| 2014/0193433 A1 | 7/2014 | Borges et al. |
| 2014/0220014 A1 | 7/2014 | Dillon et al. |
| 2016/0131654 A1 | 5/2016 | Berenson et al. |
| 2016/0331754 A1 | 11/2016 | Dansey et al. |
| 2017/0106003 A1 | 4/2017 | Berenson |
| 2017/0224730 A1 | 8/2017 | Berenson |
| 2017/0239351 A1 | 8/2017 | Hamdy et al. |
| 2018/0080085 A1 | 3/2018 | Pockaj et al. |
| 2018/0306791 A1 | 10/2018 | Bounds et al. |
| 2019/0049437 A1 | 2/2019 | Berenson |
| 2019/0107541 A1 | 4/2019 | Berenson et al. |
| 2020/0326339 A1 | 10/2020 | Berenson |
| 2022/0000872 A1 | 1/2022 | Berenson et al. |

FOREIGN PATENT DOCUMENTS

| | | |
|---|---|---|
| CN | 102421801 A | 4/2012 |
| EP | 0937461 B1 | 7/2005 |
| EP | 2762496 A1 | 8/2014 |
| JP | 2019501369 A | 1/2019 |
| WO | WO 2002/068414 A2 | 9/2002 |
| WO | WO 2004/081043 A2 | 9/2004 |
| WO | WO 2006/044582 A2 | 4/2006 |
| WO | WO 2007/131092 A2 | 11/2007 |
| WO | WO 2010/104949 A2 | 9/2010 |
| WO | WO 2012/163805 A1 | 12/2012 |
| WO | WO 2014/068079 A1 | 5/2014 |
| WO | WO 2014/124280 A1 | 8/2014 |

(Continued)

OTHER PUBLICATIONS

Carpenter et al, B-cell Maturation Antigen is a Promising Target for Adoptive T-cell Therapy of Multiple Myeloma, 2013, Clin Cancer Res., 19(8):2048-2060 (Year: 2013).*
Tockman et al, Considerations in Bringing a Cancer Biomarker to Clinical Application, 1992, Cancer Research, 52, p. 2711s-2718s (Year: 1992).*
Ali et al. (Abstract P1-02-10; Presented at: San Antonio Breast Cancer Symposium; Dec. 6-10, 2016; San Antonio, TX) (Year: 2016).*
Bahadir et al, Lateral flow assays: Principles, designs, and labels, Analytical Chemistry, 2016, p. 286-306 (Year: 2016).*
R&D Systems, Inc., Quantikine ELISA Human CYR61/CCN1 Immunoassay, 2014, 16 pages (Year: 2014).*
Dou et al, April, BCMA, and TACI proteins are abnormally expressed in non-small cell lung cancer, 2016, Oncology Letters, 12: 3351-3355 (Year: 2016).*

(Continued)

*Primary Examiner* — Mark Halvorson
*Assistant Examiner* — Dennis J Sullivan
(74) *Attorney, Agent, or Firm* — Stites & Harbison, PLLC; Mandy Wilson Decker

(57) ABSTRACT

The compositions and methods of the invention relate generally to detection of biomarkers for the diagnosis, prognosis, and monitoring of solid tumor cancers. In particular, the invention relates to compositions and methods for detection of B-cell maturation antigen (BCMA) for the diagnosis, prognosis, and monitoring of solid tumor type of cancers.

19 Claims, 6 Drawing Sheets
Specification includes a Sequence Listing.

(56) References Cited

FOREIGN PATENT DOCUMENTS

| WO | WO 2015/166073 A1 | 11/2015 |
|----|----|----|
| WO | WO-2016061142 A1 | 4/2016 |
| WO | WO 2016/090320 A1 | 6/2016 |
| WO | WO 2017/019496 A1 | 2/2017 |
| WO | WO-2017031104 A1 | 2/2017 |
| WO | WO-2017072716 A1 | 5/2017 |
| WO | WO 2017/123741 A1 | 7/2017 |
| WO | WO 2017/201040 A1 | 11/2017 |
| WO | WO-2018026819 A2 | 2/2018 |
| WO | WO 2018/231944 A1 | 12/2018 |
| WO | WO-2019018603 A2 | 1/2019 |
| WO | WO-2020092792 A2 | 5/2020 |

OTHER PUBLICATIONS

Abdelgawad, et al., "Significance of Proliferation Markers and Prognostic Factors in Egyptian Patients with Multiple Myeloma". Asian Pacific Journal of Cancer Prevention (2016); 17(3): 1351-1355.
Avrameas, et al., "Coupling of Enzymes to Antibodies and Antigens." Scand. J Immunol. (1978); vol. 8 Suppl. 7: 7-23.
Bellucci, et al., "Graft-versus-tumor response in patients with multiple myeloma is associated with antibody response to BCMA, a plasma-cell membrane receptor." Blood (2005); 105(10): 3945-3950.
Benboubker, et al., "A new serologic index for low-grade non-Hodgkin's lymphoma based on initial CA125 and LDH serum levels." Annals of Oncology (2000); 11:1485-1491.
Bladé, J., et al., "Criteria for evaluating disease response and progression in patients with multiple myeloma treated by high-dose therapy and haemopoietic stem cell transplantation. Myeloma Subcommittee of the EBMT. European Group for Blood and Marrow Transplant." Br J Haematol. (1998); 102(5): 1115-1123.
Boerner, et al., "Production of antigen-specific human monoclonal antibodies from in vitro-primed human splenocytes," J. Immunol. (1991); 147 (1): 86-95.
Borges, et al., "Chorioallantoic Membrane Angiogenesis Model for Tissue Engineering: A New Twist on a Classic Model." Tissue Engineering (2003); 9 (3): 441-450.
Campbell and Berenson, "Animal Models of Multiple Myeloma and Their Utility in Drug Discovery," Current Protocols in Pharmacology Chapter 14, Unit 14.9.1, Supplement 40 (Mar. 2008).
Cheema, et al., "Elevated Serum B Lymphocyte Stimulator Levels in Patients With Systemic Immune-Based Rheumatic Diseases" Arthritis & Rheumatism, 44(6):1313-1319 (2001).
Chiu, et al., "Hodgkin lymphoma cells express TACI and BCMA receptors and generate survival and proliferation signals in response to BAFF and APRIL," Blood (2007); 109 (2): 729-739.
Chiu, et al., "The TNF family members BAFF and APRIL play an important role in Hodgkin lymphoma." Blood (2005); 106 (11, part 1): pp. 11A), BIOSIS Accession No. 2006:180280, 47th Annual Meeting of the American Society of Hematology, Dec. 10-13, 2005, Meeting Abstract, 2 pages.
Chou and Talalay, "Quantitative analysis of dose-effect relationships: the combined effects of multiple drugs or enzyme inhibitors." Adv Enzyme Regul. (1984); 22: 27-55.
Christiansen, et al., "Serum Levels of Soluble Intercellular Adhesion Molecule 1 Are Increased in Chronic B-Lymphocytic Leukemia and Correlate With Clinical Stage and Prognostic Markers," Blood (1994); 84 (9): 3010-3016.
Chuaqui, et al., "Post-analysis follow-up and validation of microarray experiments," Nature Genetics (2002); Supplement 32: 509-514.
Churchill, "Fundamentals of experimental design for CDNA microarrays," Nature Genetics (2002); Supplement 32: 490-495.
Clackson, et al., "Making antibody fragments using phage display libraries," Nature (1991); 352: 624-628.

Database Medline [Online] US National Library of Medicine (NLM), Bethesda, MD, US; Mar. 2016 (Mar. 2013), Abdelgawad, Iman A., et al., "Significance of Some Proliferation Markers and Some Prognostic Factors in Patients with Multiple Myeloma and their Impact on the Patients' Survival", Database accession No. NLM27268602 & Abdelgawad, et al., "Significance of Proliferation Markers and Prognostic Factors in Egyptian Patients with Multiple Myeloma". Asian Pac J Cancer Prev. (2016); 17(3): 1351-1355, 1 page.
Day, et al., "Selectivity of BAFF/BLyS and APRIL for binding to the TNF family receptors BAFFR/BR3 and BCMA," Biochemistry (2005); 44:1919-1931.
Deshayes, et al., "Abnormal production of the TNF-homologue APRIL increases the proliferation of human malignant glioblastoma cell lines via a specific receptor." Oncogene (2004); 23 (17): 3005-3012.
Durie, B.G.M., et al. "International uniform response criteria for multiple myeloma." Leukemia (2006); 20 (9): 1467-1473.
Elsawa, et al., "B-lymphocyte stimulator (BLyS) stimulates immunoglobulin production and malignant B-cell growth in Waldenström macroglobulinemia." Blood (2006); 107 (7): 2882-2888.
EP Application No. 14748765.6, Supplementary European Search Report dated Aug. 2, 2016, 7 pages.
EP Application No. 15800211.3, Partial Supplementary European Search Report dated Dec. 14, 2017, 10 pages.
EP Application No. 15800211.3, Supplementary European Search Report dated Dec. 12, 2017, 21 pages.
EP Application No. 15807258.7, Extended European Search Report dated Jan. 4, 2018, 11 pages.
EP Application No. 17738918.6, Extended European Search Report dated Jun. 6, 2019, 11 pages.
EP Application No. 17800006.3, Partial Supplementary European Search Report dated Jan. 20, 2010, 17 pages.
Fragioudaki, et al., "B cell-activating factor: its clinical significance in multiple myeloma patients". Annals of Hematology (Sep. 2012); 91(9): 1413-1418. Epub Apr. 21, 2012.
Fragioudaki, et al., "Serum BAFF levels are related to angiogenesis and prognosis in patients with multiple myeloma". Leukemia Research (Aug. 2012); 36(8): 1004-1008. Epub Apr. 10, 2012.
Gabrilovic, et al., "Myeloid-derived suppressor cells". Cancer Immunol Res. (Jan. 2017); 5(1): 3-8.
Ghermezi, et al., "Serum B-cell maturation antigen: a novel biomarker to predict outcomes for multiple myeloma patients." Haematologica (2017); 102 (4): 785-795. Epub Dec. 29, 2016.
Gordon, et al., "Identification of Novel Receptors on Myeloma Cells and Monocytes That Contribute to Myeloma Tumor Proliferation and Angiogenesis." Blood (2005); 106 (11): 2507.
Gras, et al., "BCMAp: an integral membrane protein in the Golgi apparatus of human mature B lymphocytes," International Immunology (1995); 7 (7): 1093-1106.
Greipp, et al., "International Staging System for Multiple Myeloma." Journal of Clinical Oncology (2005); 23(15): 3412-3420.
Groom, et al., "Association of BAFF/BLyS overexpression and altered B cell differentiation with Sjögren's syndrome," Journal of Clinical Investigation (2002); 109 (1): 59-68.
Gross, et al., "TACI and BCMA are receptors for a TNF homologue implicated in B-cell autoimmune disease," Nature (2000); 404: 995-999.
Hamblin and Hamblin, "The Immunodeficiency of Chronic Lymphocytic Leukaemia," British Medical Bulletin (2008); 87 (1): 49-62.
Holloway et al., "Options available—from start to finish—for obtaining data from DNA Microarrays II," Nature Genetics (2002); Supplement 32: 481-489.
Hoogenboom, et al., "By-passing Immunisation Human Antibodies from Synthetic Repertoires of Germline VH Gene Segments Rearranged in Vitro," J. Mol. Biol. (1992); 227: 381-388.
Hornbeck, et al., "Enzyme-Linked Immunosorbent Assays (ELISA)." Current Protocols in Molecular Biology (1991), 11.2.1-11.2.22, 22 pages.

(56) References Cited

OTHER PUBLICATIONS

Huerta-Yepez, et al., "Overexpression and Preferential Nuclear Translocation of the Transcription Factor Yin Yang 1 (YY1) in Human Bone Marrow-Derived Multiple Myeloma." Blood (2005); 106 (11): 3394.
International Preliminary Report on Patentability for International Application No. PCT/US2009/063316, dated May 10, 2011, 5 pages.
International Preliminary Report on Patentability for International Application No. PCT/US2014/015338, dated Aug. 11, 2015, 8 pages.
International Preliminary Report on Patentability for International Application No. PCT/US2015/032869, dated Nov. 29, 2016, 8 pages.
International Preliminary Report on Patentability for International Application No. PCT/US2015/035023, dated Dec. 15, 2016, 5 pages.
International Preliminary Report on Patentability for International Application No. PCT/US2016/043536, dated Jan. 30, 2018, 5 pages.
International Preliminary Report on Patentability for International Application No. PCT/US2017/013169, dated Jul. 17, 2018, 6 pages.
International Preliminary Report on Patentability for International Application No. PCT/US2017/032894, dated Nov. 20, 2018, 6 pages.
International Preliminary Report on Patentability for International Application No. PCT/US2018/037275, dated Dec. 17, 2019, 10 pages.
International Search Report and Written Opinion for International Application No. PCT/US2009/063316, dated Feb. 3, 2010, 8 pages.
International Search Report and Written Opinion for International Application No. PCT/US2014/015338, dated Jul. 16, 2014, 11 pages.
International Search Report and Written Opinion for International Application No. PCT/US2015/035023, dated Sep. 22, 2015, 7 pages.
International Search Report and Written Opinion for International Application No. PCT/US2016/043536, dated Oct. 7, 2016, 7 pages.
International Search Report and Written Opinion for International Application No. PCT/US2017/013169, dated Apr. 10, 2017, 8 pages.
International Search Report and Written Opinion for International Application No. PCT/US2017/032894, dated Aug. 29, 2017, 8 pages.
International Search Report and Written Opinion for International Application No. PCT/US2018/037275, dated Oct. 26, 2018, 15 pages.
International Search Report and Written Opinion, for International Application No. PCT/US2015/032869, dated Aug. 7, 2015, 10 pages.
Invitation to Pay Additional Fees for International Application No. PCT/US2014/015338, dated Apr. 21, 2014, 2 pages.
Invitation to Pay Additional Fees for International Application No. PCT/US2018/037275, dated Aug. 27, 2018, 2 pages.
Iris, et al., "Prevention Of Minimal Residual Disease In Ph plus AL", Database accession No. PREV201400360357, Database Biosis [Online], Biosciences Information Service, Philadelphia, PA, US, Nov. 2013; & Blood, vol. 122, No. 21, Nov. 2013 (Nov. 2013), p. 1265, 55th Annual Meeting of the American Society of Hematology; New Orleans, LA, USA, Dec. 7-10, 2013, ISSN: 0006-4971 (print).
Jäger, et al., "Serum levels of the angiogenic factor pleiotrophin in relation to disease stage in lung cancer patients." British Journal of Cancer (2002); 86 (6): 858-863.
Jones, et al., "Replacing the complementarity-determining regions in a human antibody with those from a mouse," Nature (1986); 321: 522-525.
Jones, et al., "The soluble interleukin 6 receptor: mechanisms of production and implications in disease," FASEB J. (2001); 15: 43-58.
Källander, et al., "Serum deoxythymidine kinase gives prognostic information in chronic lymphocytic leukemia." Cancer (1984); 54 (11): 2450-2455.
Karpusas, et al., "Crystal structure of extracellular human BAFF, a TNF family member that stimulates B lymphocytes." Journal of Molecular Biology (2002); 315(5): 1145-1154.
Kawasaki, et al., "Presence of four major haplotypes in human BCMA gene: lack of association with systemic lupus erythematosus and rheumatoid arthritis," Genes and Immunity (2001); 2: 276-279.
Kohler, et al., "Continuous cultures of fused cells secreting antibody of predefined specificity," Nature (1975); 256: 495-497.
Kreuzaler, et al., "Soluble BAFF Levels Inversely Correlate with Peripheral B Cell Numbers and the Expression of BAFF Receptors". The Journal of Immunology (Jan. 1, 2012); 188(1): 497-503. Epub Nov. 28, 2011.
Kyle and Rajkumar, "Criteria for diagnosis, staging, risk stratification and response assessment of multiple myeloma." Leukemia (2009); 23(1): 3-9.
Kyle, Robert A., "The Monoclonal Gammopathies," Clinical Chemistry (1994); 40/11 (B): 2154-2161.
Laabi, et al., "A new gene, BCM, on chromosome 16 is fused to the interleukin 2 gene by a t(4;16)(q26;p13) translocation in a malignant T cell lymphoma," The EMBO Journal (1992); 11(11): 3897-3904.
Laabi, et al., "The BCMA gene, preferentially expressed during B lymphoid maturation, is bidirectionally transcribed," Nucleic Acids Research (1994); 22 (7): 1147-1154.
Laras, et al., "Substituted thiazolamide coupled to a redox delivery system: a new γ-secretase inhibitor with enhanced pharmacokinetic profile." Org. Biomol. Chem. (2005); 3: 612-618.
Laurent, et al., "γ-secretase directly sheds the survival receptor BCMA from plasma cells." Nature Communications (2015); 6: 7333, 12 pages.
Lee, et al., "Prognosis of Chronic Lymphocytic Leukemia: A Multivariate Regression Analysis of 325 Untreated Patients." Blood (1987); 69 (3): 929-936.
Lemancewicz, et al., "Evaluation of TNF superfamily molecules in multiple myeloma patients: Correlation with biological and clinical features", Leukemia Research (Sep. 2013); 37(9): 1089-1093. Epub Jun. 12, 2013.
Li, et al., "The Pro-angiogenic Cytokine Pleiotrophin Potentiates Cardiomyocyte Apoptosis through Inhibition of Endogenous AKT/PKB Activity." The Journal of Biological Chemistry (2007); 282 (48): 34984-34993.
Liu, T., et al., "Interleukin-6 and JAK2/STAT3 signaling mediate the reversion of dexamethasone resistance after dexamethasone withdrawal in 7TD1 multiple myeloma cells." Leukemia Research (2013); 37(10): 1322-1328.
Mackay, et al., "Mice Transgenic for BAFF Develop Lymphocytic Disorders Along with Autoimmune Manifestations," J. Exp. Med., 190(11):1697-1710 (1999).
Madry, et al., "The characterization of murine BCMA gene defines it as a new member of the tumor necrosis factor receptor superfamily," International Immunology (1998); 10(11): 1693-1702.
Marks, et al., "By-passing Immunization Human Antibodies from V-gene Libraries Displayed on Phage," J. Mol. Biol., 222: 581-597 (1991).
McLendon, et al., "Cell-free assays for γ-secretase activity." The FASEB Journal (2000); 14 (15): 2383-2386.
Moreaux, et al., "BAFF and APRIL protect myeloma cells from apoptosis induced by interleukin 6 deprivation and dexamethasone." Blood (2004); 103(8): 3148-3157.
Morrison, et al., "Chimeric human antibody molecules: Mouse antigen-binding domains with human constant region domains." Proc. Natl. Acad. Sci. USA (1984); 81: 6851-6855.
Mukhopadhyay, et al., "Identification and Characterization of A Novel Cytokine, THANK, a TNF Homologue That Activates Apoptosis, Nuclear Factor-kB, and c-Jun NH2-Terminal Kinase." J. Biol. Chem. (1999); 274 (23): 15978-15981.
Muramatsu, T., "Midkine and Pleiotrophin: Two Related Proteins Involved in Development, Survival, Inflammation and Tumorigenesis." The Journal of Biochemistry (2002); 132 (3): 359-371.

(56) References Cited

OTHER PUBLICATIONS

Novak, et al., "Expression of BCMA, TACI, and BAFF-R in multiple myeloma: a mechanism for growth and survival." Blood (2004); 103 (2): 689-694.
O'Connor, et al., "BCMA Is Essential for the Survival of Long-lived Bone Marrow Plasma Cells". Journal of Experimental Medicine (2004); 199(1): 91-97.
Palumbo, A., et al., "Lenalidomide in combination with dexamethasone for the treatment of relapsed or refractory multiple myeloma." Blood Reviews (2009); 23 (2): 87-93.
PCT/US2019/059199, International Search Report and Written Opinion dated Jan. 14, 2020, 9 pages.
Pelekanou, et al., "BAFF, APRIL, TWEAK, BCMA, TACI and Fn14 proteins are related to human glioma tumor grade: immunohistochemistry and public microarray data meta-analysis." PLoS One (2013); 8 (12):e83250, and Supplementary Data, Table S2, 12 pages.
Pemovska, T., et al., "Individualized Systems Medicine Strategy to Tailor Treatments for Patients with Chemorefractory Acute Myeloid Leukemia." Cancer Discovery (2013); 13 (12): 1416-1429.
Pemovska, T., et al., "Individualized Systems Medicine Strategy to Tailor Treatments for Patients with Chemorefractory Acute Myeloid Leukemia." Cancer Discovery (2013); 13 (12): 1416-1429; Supplementary Materials. DOI: 10.1158/2159-8290.CD-13-0350 URL:http://cancerdiscovery.aacrjournals.org/content/candisc/suppl/2013/09/18/2159-8290.CD-13-0350.DC1/supp_figs_tables_and_methods.pdf.
Picarda, et al., "Molecular Pathways: Targeting B7-H3 (CD276) for Human Cancer Immunotherapy". Clin Cancer Res. (Jul. 15, 2016); 22(14): 3425-3431. Epub May 20, 2016.
Ponticelli, et al., "Modulation of Angiogenesis by a Tetrameric Tripeptide That Antagonizes Vascular Endothelial Growth Factor Receptor." The Journal of Biological Chemistry (2008); 283 (49): 34250-34259.
Prasad, et al., Discovery of (S)-2-((S)-2-(3,5-difluorophenyl)-2-hydroxyacetamido)-N-((S,Z)-3-methyl-4-oxo-4,5-dihydro-3Hbenzo[d][1,2]diazepin-5-yl)propanamide (BMS-433796): A γ-secretase inhibitor with Aβ lowering activity in a transgenic mouse model of Alzheimer's disease Bioorganic & Medicinal Chemistry Letters (2007); 17: 4006-4011.
Presta, Leonard G., "Antibody engineering," Current Opinion in Structural Biology (1992); 2: 593-596.
Pufe, et al., "Expression of pleiotrophin, an embryonic growth and differentiation factor, in rheumatoid arthritis." Arthritis & Rheumatism (2003); 48 (3): 660-667.
Purdue et al., "Pre-diagnostic serum levels of cytokines and other immune markers and risk of non-Hodgkin lymphoma." Cancer Res. (2011); 71 (14): 4898-4907.
Quackenbush, John, "Microarray data normalization and transformation." Nature Genetics (2002); Supp. 32: 496-501.
Rajkumar, et al., "Consensus recommendations for the uniform reporting of clinical trials: report of the International Myeloma Workshop Consensus Panel 1." Blood (2011); 117 (18):4691-4695.
Rennert, et al., "A soluble Form of B Cell Maturation Antigen, a Receptor for the Tumor Necrosis Factor Family Member APRIL, Inhibits Tumor Cell Growth." J. Exp. Med. (2000); 192 (11): 1677-1683.
Riechmann et al., "Reshaping human antibodies for therapy," Nature (1988); 332: 323-327.
Rihacek, et al., "B-Cell Activating Factor as a Cancer Biomarker and Its Implications in Cancer-Related Cachexia." Biomed Res Int. (2015); 2015: 792187. Epub Aug. 3, 2015.
Rodwell and McKearn, "Linker Technology: Antibody-Mediated Delivery Systems." Biotechnology (1985); 3: 889-894.
Sanchez, et al., "Circulating Bcma Binding to Its Ligand BAFF Prevents Normal Antibody Production in Multiple Myeloma Patients." Blood (2014); 124: 4713.
Sanchez, et al., "Soluble B-Cell Maturation Antigen Mediates Tumor-Induced Immune Deficiency in Multiple Myeloma." Clin Cancer Res. (Jul. 2016); 22(13): 3383-3397. Epub Mar. 9, 2016.
Sanchez, et al., "Soluble Bcma in Myeloma Serum Binds Its Ligands BAFF and Prevents Normal Antibody Production in Multiple Myeloma Patients." Blood (2015); 126: 1799.
Sanchez, et al., "Serum B-cell maturation antigen is elevated in multiple myeloma and correlates with disease status and survival," British Journal of Haematology (2012); 158 (6): 727-738.
Sanchez, et al., BIOSIS Accession No. 2013:233275, "Serum Levels of B-Cell Maturation Antigen Are Elevated in Multiple Myeloma Patients and Correlate with Disease Status and Overall Survival." Blood (2012); 120 (21): 4026.
Sarfati, et al., "Elevation of IgE-Binding Factors in Serum of Patients With B Cell-Derived Chronic Lymphocytic Leukemia," Blood (1988); 71 (1): 94-98.
Schneider, et al., "BAFF, a Novel Ligand of the Tumor Necrosis Factor Family, Stimulates B Cell Growth," J. Exp. Med. (1999); 189 (11): 1747-1756.
Seshasayee, et al., "Loss of TACI Causes Fatal Lymphoproliferation and Autoimmunity, Establishing TACI as an Inhibitory BLyS Receptor," Immunity (2003); 18: 279-288.
Sharada, et al., "Intravenous dexamethasone pulse therapy in diffuse systemic sclerosis. A randomized placebo-controlled study." Rheumatology International (1994); 14 (3): 91-94.
Shu, et al., "TALL-1 is a novel member of the TNF family that is down-regulated by mitogens," Journal of Leukocyte Biology (1999); 65 (5): 680-683.
Simonsson, et al., "b 2-Microglobulin in Chronic Lymphocytic Leukaemia." Scand J Haematol (1980); 24 (2): 174-180.
Slonim, Donna K., "From patterns to pathways: gene expression data analysis comes of age." (2002) Nature Genetics (2002); Suppl. 32: 502-508.
Smith, et al., "The TNF Receptor Superfamily of Cellular and Viral Proteins: Activation, Costimulation, and Death." Cell (1994); 76: 959-962.
Stephens, et al., "An intermediate-risk multiple myeloma subgroup is defined by sIL-6r: levels synergistically increase with incidence of SNP rs2228145 and 1q21 amplification." Blood (2012); 119 (2): 503-512.
Syn, et al., "De-novo and acquired resistance to immune checkpoint targeting". Lancet Oncol. (Dec. 2017); 18(12): e731-e741.
The International Myeloma Working Group, "Criteria for the classification of monoclonal gammopathies, multiple myeloma and related disorders: a report of the International Myeloma Working Group." British Journal of Haematology (2003); 121 (5): 749-757.
Thompson, et al., "BAFF Binds to the Tumor Necrosis Factor Receptor-like Molecule B Cell Maturation Antigen and Is Important for Maintaining the Peripheral B Cell Population." J. Exp. Med. (2000); 192 (1): 129-135.
Thompson, et al., "BAFF-R, a Newly Identified TNF Receptor That Specifically Interacts with BAFF." Science (2001); 293: 2108-2111.
Van Oers, et al., "Expression and Release of CD27 in Human B-Cell Malignancies." Blood (1993); 82(11): 3430-3436.
Vardanyan, et al., "Serum Levels of B-Cell Maturation Antigen Are Elevated in Waldenström's Macroglobulinemia Patients and Correlate with Disease Status and Conventional M-Protein and IgM Levels". Blood (Dec. 3, 2015); 126(23): 1778.
Varfolomeev, et al., "APRIL-Deficient Mice Have Normal Immune System Development." Molecular and Cellular Biology (2004); 24 (3): 997-1006.
Wu, et al., "Tumour Necrosis Factor (TNF) Receptor Superfamily Member TACI Is a High Affinity Receptor for TNF Family Members APRIL and BLyS." Journal of Biological Chemistry (2000); 275(45): 35478-35485.
Xu, et al., "B-Cell Maturation Protein, Which Binds the Tumour Necrosis Factor Family Members BAFF and APRIL, Is Dispensable for Humoral Immune Responses." Molecular and Cellular Biology (2001); 21 (12): 4067-4074.
Yan, et al., "Identification of a novel receptor for B lymphocyte stimulator that is mutated in a mouse strain with severe B cell deficiency." Current Biology (2001); 11: 1547-1552.
Yu, et al., "APRIL and TALL-1 and receptors BCMA and TACI: system for regulating humoral immunity." Nature Immunology (2000); 1 (3): 252-256.

(56) References Cited

OTHER PUBLICATIONS

Zhang, et al., "B Cell-Activating Factor as a New Potential Marker in Inflammatory Bowel Disease". Digestive Diseases and Sciences (Sep. 2016); 61(9): 2608-2618. Epub Apr. 7, 2016.
Zhang, et al., "Cutting Edge: A Role for B Lymphocyte Stimulator in Systemic Lupus Erythematosus." The Journal of Immunology (2001); 166: 6-10.
Berenson, et al., "A Phase I Study of Ruxolitinib, Lenalidomide, and Steroids for Patients with Relapsed/Refractory Multiple Myeloma". Clin. Cancer Res. (May 2020); 26(10): 2346-2353. Epub Jan. 14, 2020.
Boasso, et al., "Immune dysregulation in human immunodeficiency virus infection: know it, fix it, prevent it", J Intern Med. (Jan. 2009); 265(1): 78-96.
Carbone, et al., "Potential role of serum BAFF as a biomarker in HIV infection", Infectious Diseases (2015); 47(4): 260-262. Epub Feb. 17, 2015.
Concise Medical Dictionary, 8th ed., "serum", Oxford University Press, Year: 2010, 1 page.
EP Application No. 17800006.3, Extended European Search Report dated Jun. 25, 2020, 16 pages.
EP Application No. 18818048.3, Extended European Search Report dated Mar. 17, 2021, 9 pages.
Gu, et al., "Notch signaling: its roles and therapeutic potential in hematological malignancies". Oncotarget (May 17, 2016); 7(20): 29804-29823.
Holthof and Mutis, "Challenges for Immunotherapy in Multiple Myeloma: Bone Marrow Microenvironment-Mediated Immune Suppression and Immune Resistance". Cancers (Basel) (Apr. 17, 2020); 12(4): 988, 15 pages.
Huntington, Nicholas D., "A BAFF antagonist suppresses experimental autoimmune encephalomyelitis by targeting cell-mediated and humoral immune responses." International Immunology (Oct. 2006); 18(10): 1473-1485.
International Preliminary Report on Patentability for International Application No. PCT/US2019/059199, dated Apr. 27, 2021, 5 pages.
Maglione, Paul J., "Serum B-Cell Maturation Antigen (BCMA) Levels Differentiate Primary Antibody Deficiencies." Journal of Allergy and Clinical Immunology Practice(Jan. 2020); 8(1): 283-291, e1.
Maglione, Paul J., "Reduced serum BCMA levels distinguish patients with primary antibody deficiency." Journal of Immunology (May 1, 2016); 196(Supp. 1), p. 193.7.
Moir, Susan, "Decreased survival of B cells of HIV-viremic patients mediated by altered expression of receptors of the TNF superfamily". Journal of Experimental Medicine (2004); 200(5): 587-599.
Rodriguez, et al., Plasma levels of B-lymphocyte stimulator increase with HIV disease progression, AIDS (Sep. 5, 2003); 17(13): 1983-1985.
Rong, Jin, "Age-related changes in BAFF and APRIL profiles and upregulation of BAFF and APRIL expression in patients with primary antibody deficiency." Int J Mol Med (Feb. 2008); 21(2): 233-238.
Sanchez, Eric, "The clinical significance of B-cell maturation antigen as a therapeutic target and biomarker." Expert Rev Mal Diagn (Mar. 7, 2018); 18(4): 319-329.
Shaker, Olfat G., "Expression of TNF-, April and BCMA in Behcet's Disease." Journal of Immunology Research (Nov. 5, 2014); vol. 2014, 380405, 7 pages.
Shih and Wang, "Notch Signaling, γ Secretase Inhibitors, and Cancer Therapy". Cancer Res (2007); 67(5): 1879-1882.
Torzewski, et al., "Animal Models of C-Reactive Protein". Hindawi Publishing Corporation, Mediators of Inflammation, vol. 2014, Article ID 683598, 2014, pp. 1-7.
Van Der Vekens, et al., "Human and equine cardiovascular endocrinology: beware to compare". Cardiovascular Endocrinology (Dec. 2013); 2(4): 67-76.
Byrne Michael et al., "Leveraging JAK-STAT regulation in myelofibrosis to improve outcomes with allogeneic hematopoietic stem-cell transplant", The Rapeutic Advances in Hematology, vol. 9, No. 9, Sep. 1, 2018 (Sep. 1, 2018 ), pp. 251-259, Retrieved from the Internet:URL:http://journals.sagepub.com/doi/full-XML/10.1177/2040620718786437.
Debureaux P.E., et al., "Nivolumab combined with ruxolitinib: antagonism or synergy", Annals of Oncology, vol. 29, No. 5, May 1, 2018 (May 1, 2018 ), pp. 1333-1334.
Jianxuan Zou et al., "Immunotherapy based on bispecific T-cell engager with hIgG1 Fe sequence as a new therapeutic strategy in multiple myeloma", Cancer Science, vol. 106, No. 5,Mar. 13, 2015 (Mar. 13, 2015), pp. 512-521.
Jin et al., "Age-related changes in BAFF and APRIL profiles and upregulation of BAFF and APRIL expression in patients with primary antibody deficiency," International J. Mol. Med., 2008, vol. 21, pp. 233-238.
Kenderian, S. S., et al., "Ruxolitinib Prevents Cytokine Release Syndrome after Car T-Cell Therapy Without Impairing the Anti-Tumor Effect in a Xenograft Model", Biology of Blood and Marrow Transplantation, vol. 23, No. 3, 2017, pp. S19-S20.
Ma Jing et al., "Immunotherapy Strategies Against Multiple Myeloma", Technology in Cancer Research and Treatment, vol. 16, No. 6, Dec. 1, 2017 (Dec. 1, 2017), pp. 717-726, Retrieved from the Internet:URL:https://www.ncbi.nlm.nih.gov/pmc/articles/PMC5762093/pdf/10.1177_1533034617743155.pdf.
Nijland Marcel et al., "Combined PD-1 and JAK1/2 inhibition in refractory primary mediastinal B-cell lymphoma" Annals of Hematology, Berlin, DE, vol. 97, No. 5, Jan. 11, 2018 (Jan. 11, 2018 ), pp. 905-907.
O'Farrell, Brendan, Evolution in Lateral Flow-based Immunoasssay Systems, Lateral Flow Immunoassay, Oct. 31, 2008; pp. 1-33 . (Year: 2008).
Salzer, U, et al., "Screening of functional and positional candidate genes in familieswith common variable immunodeficiency" BMC Immunology, 2008, vol. 9, 9 pages.
Tempfer, C. B., et al., "Thalidomide and lenalidomide for recurrent ovarian cancer: A systematic review of the literature", Oncology Letters, vol. 14, No. 3, Sep. 15, 2017 (Sep. 15, 2017), pp. 3327-3336.

\* cited by examiner

SEQUENCE LISTING

<160> NUMBER OF SEQ ID NOS: 2

<210> SEQ ID NO 1
<211> LENGTH: 54
<212> TYPE: PRT
<213> ORGANISM: Homo sapiens

<400> SEQUENCE: 1

```
Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
                20              25                  30

Pro Pro Leu Thr Cys Gln Arg Tyr Cys Asn Ala Ser Val Thr Asn Ser
            35              40              45

Val Lys Gly Thr Asn Ala
    50

<210> SEQ ID NO 2
<211> LENGTH: 184
<212> TYPE: PRT
<213> ORGANISM: Homo sapiens

<400> SEQUENCE: 2

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
                20              25                  30

Pro Pro Leu Thr Cys Gln Arg Tyr Cys Asn Ala Ser Val Thr Asn Ser
            35              40              45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70              75                  80

Asn Ser Glu Pro Leu Lys Asp Glu Phe Lys Asn Thr Gly Ser Gly Leu
            85              90                  95

Leu Gly Met Ala Asn Ile Asp Leu Glu Lys Ser Arg Thr Gly Asp Glu
            100             105                 110

Ile Ile Leu Pro Arg Gly Leu Glu Tyr Thr Val Glu Glu Cys Thr Cys
            115             120                 125

Glu Asp Cys Ile Lys Ser Lys Pro Lys Val Asp Ser Asp His Cys Phe
    130             135                 140

Pro Leu Pro Ala Met Glu Glu Gly Ala Thr Ile Leu Val Thr Thr Lys
145             150                 155                 160

Thr Asn Asp Tyr Cys Lys Ser Leu Pro Ala Ala Leu Ser Ala Thr Glu
                165             170                 175

Ile Glu Lys Ser Ile Ser Ala Arg
            180
```

DIAGNOSTIC, PROGNOSTIC, AND MONITORING METHODS FOR SOLID TUMOR CANCERS

STATEMENT REGARDING SEQUENCE LISTING

This application is a National Stage application, filed pursuant to 35 U.S.C. § 371, of International Application No. PCT/US2018/037275, filed on Jun. 13, 2018, which claims the benefit under 35 U.S.C. § 119(e) of U.S. Provisional Application No. 62/518,734, filed on Jun. 13, 2017, which is hereby incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is ONTR_002_01WO_SeqList_ST25.txt. The text file is 2 KB, was created on Jun. 12, 2018, and is being submitted electronically via EFS-Web.

FIELD OF THE INVENTION

The invention relates generally to prognosis, diagnosis, treatment, and monitoring of solid tumor cancers. In particular, the invention relates use of protein biomarkers in the prognosis, diagnosis, treatment, and monitoring of solid tumor cancers.

BACKGROUND

Tumor necrosis factor receptor superfamily, member 17 (TNFRSF17, also designated as B-cell maturation antigen (BCMA) or CD269) is a receptor that was first identified in a T-cell tumor line (Laabi et al., 1992) and subsequently shown to be expressed in B lymphocytes as they mature (Laabi et al., 1994). BCMA ligands include BAFF (B cell-activating factor; TNFSF13B) and APRIL (a proliferation-inducing ligand; TNFSF13) (Rennert et al., 2000; Thompson et al., 2000). In multiple myeloma (MM) cell lines, these ligands activate cell proliferation pathways and upregulate anti-apoptotic proteins (Moreaux et al., 2004). Both ligands also bind the receptor TACI (transmembrane activator and CAML interactor; TNFRSF13B) (Gross et al., 2000; Wu et al., 2000; Yu et al., 2000). Additionally, BAFF binds to a third receptor, called BAFF-receptor (BAFFR; TNFRSF13C), whereas APRIL does not (Thompson et al., 2001; Day et al., 2005). The ligands BAFF and APRIL are members of the tumor necrosis family (TNF) and binding of TNF members to their receptors can lead to apoptosis, differentiation or proliferation (Smith et al., 1994).

BCMA has been shown to be located on plasma cell lines (Laabi et al., 1992, 1994). Surface expression of BCMA was found on human tonsilar B-cells (Thompson et al., 2000), and on human CD138-expressing MM cells (Novak et al., 2004). Malignant cells from Hodgkin lymphoma and Waldenstrom macroglobulinemia (WM) patients also express this protein (Elsawa et al., 2006; Chiu et al., 2007).

The present inventors have previously demonstrated that BCMA is present in biological samples (e.g., serum) of subjects having various B-cell malignancies, e.g., multiple myeloma (MM), chronic lymphocytic leukemia (CLL), and B-cell non-Hodgkin's lymphomas (NHL) and correlates with the patient's response to therapy and overall survival (see, US2016/0131654, which is incorporated herein in its entirety). The present inventors have also previously found that levels of BCMA polypeptide or a fragment thereof in a biological sample (e.g., serum) of a subject correlate with the subject's overall immune status (see, US PCT/US2017/013169, which is incorporated herein in its entirety).

Currently, a non-invasive test to determine diagnosis, prognosis, and monitoring of a solid tumor cancer is not available, and requires biopsy of the subject's tissue or cell. However, such biopsies are time consuming and often lead to critical delays in diagnosing and treating the cancer. Additionally, a rapid and reliable determination of a subject's response to treatment is also currently not available, and would be greatly facilitated by a test that could reliably monitor a subject's response to treatment at different time points during the course of a treatment regimen. Further, existing biomarkers of solid tumor cancers do not correlate well with anti-cancer treatment, or with the extent and severity of the disease. Therefore, the art is deficient in reliable diagnostic, prognostic, and treatment monitoring biomarkers of solid tumor cancers, and there is a need in the art to design a fast, reproducible, inexpensive, and reliable test that can be used for diagnosis, prognosis and monitoring of a solid tumor cancer.

BRIEF SUMMARY OF THE INVENTION

The present disclosure generally provides compositions and methods for reliable and reproducible diagnosis, prognosis and monitoring of solid tumor cancers by detecting of an amount of BCMA in a biological sample.

In one aspect, the disclosure provides, a method of prognosis for a solid tumor type of cancer in a subject, comprising detecting an amount of BCMA polypeptide or a fragment thereof in a biological sample obtained from the subject.

In an embodiment, the amount of BCMA polypeptide or a fragment thereof in the biological sample being lower than about 30 ng/mL correlates with a reduced time to progression (TTP) of the cancer.

In an embodiment, the amount of BCMA polypeptide or a fragment thereof in the biological sample being lower than about 30 ng/mL indicates a reduced length of progression-free survival (PFS) for the subject.

In an embodiment, the amount of BCMA polypeptide or a fragment thereof in the biological sample being lower than about 15 ng/mL or higher than about 150 ng/mL indicates a reduced overall survival (OS) for the subject.

In an embodiment, the biological sample is selected from the group consisting of a serum sample, a plasma sample, a supernatant obtained from a culture of the subject's bone marrow mononuclear cells, and peripheral blood mononuclear cells. In an embodiment, the biological sample is a serum sample.

In a second aspect, the disclosure provides, a method of monitoring progression or response to treatment of solid tumor cancer, comprising detecting an amount of BCMA or a fragment thereof in a biological sample obtained from a subject diagnosed with the cancer at a time point following treatment.

In an embodiment, the amount of BCMA polypeptide or a fragment thereof in the biological sample of lower than about 30 ng/mL or higher than about 150 ng/mL indicates that the cancer will progress sooner.

In an embodiment, the amount of BCMA polypeptide or a fragment thereof in the biological sample of higher than about 30 ng/mL but lower than about 150 ng/mL indicates that the cancer is more likely to enter remission or respond to treatment.

In an embodiment, the biological sample is selected from the group consisting of a serum sample, a plasma sample, a supernatant obtained from a culture of the subject's bone marrow mononuclear cells, and peripheral blood mononuclear cells. In an embodiment, the biological sample is a serum sample.

In an embodiment, the solid tumor type of cancer is selected from the group consisting of breast cancer, astrocytoma, head and neck squamous cell cancer, squamous cell carcinoma of head and neck, brain cancer, nervous system cancer, papillary renal cell carcinoma Type II, hepatocellular carcinoma, lung cancer such as small cell lung cancer and non-small cell lung cancer, pancreatic cancer, gall bladder cancer, esophageal cancer, bladder cancer, testicular cancer, ovarian cancer, uterine cancer, colon cancer, rectal cancer, cervical cancer, thyroid cancer, epithelial cancer, esophageal carcinoma, large bowel cancer, neuroblastoma, glioblastoma, glioma, prostate cancer, ovarian cancer, endometrial cancer, stomach cancer, oral cancer, throat cancer, tracheal cancer, bone cancer, liver cancer, sarcoma, skin cancer, squamous cell carcinomas of the mouth, throat, larynx, and lung, and colorectal cancer. In an embodiment, the solid tumor cancer is breast cancer. In an embodiment, the solid tumor cancer is sarcoma. In an embodiment, the BCMA polypeptide or fragment thereof is a cleaved BCMA polypeptide. In an embodiment, the BCMA polypeptide or a fragment thereof is detected using a detection system selected from the group consisting of enzyme-linked immunosorbent assay (ELISA), radioimmunoassay (RIA), enzyme immunoassay (EIA), fluorescence immunoassay (FIA), luminescence immunoassay (LIA), lateral flow assay (LFA), and strip assay. In an embodiment, the detection system is a lateral flow assay.

In an embodiment, the detection is performed using an antibody specific for BCMA polypeptide or a fragment thereof. In an embodiment, the antibody specific for BCMA polypeptide or a fragment thereof is a monoclonal antibody. In an embodiment, the antibody specific for BCMA polypeptide or a fragment thereof is a polyclonal antibody.

In a third aspect, the disclosure provides a kit for monitoring progression or response to treatment of a solid tumor type of cancer in a subject, comprising a reagent suitable for determining levels of BCMA polypeptide or a fragment thereof in a biological sample obtained from the subject. In an embodiment, the kit comprises an antibody specific for BCMA polypeptide or fragment thereof. In an embodiment, the antibody specific for BCMA polypeptide or fragment thereof is a polyclonal antibody. In an embodiment, the antibody specific for BCMA polypeptide or fragment thereof is a monoclonal antibody. In an embodiment, the kit comprises a detection system selected from the group consisting of: ELISA assay, RIA assay, EIA assay, FIA assay, LIA assay, lateral flow assay, or strip assay.

Further aspects and embodiments of the disclosure are provided by the detailed description that follows.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed methods.

DETAILED DESCRIPTION OF THE INVENTION

Figure 1:
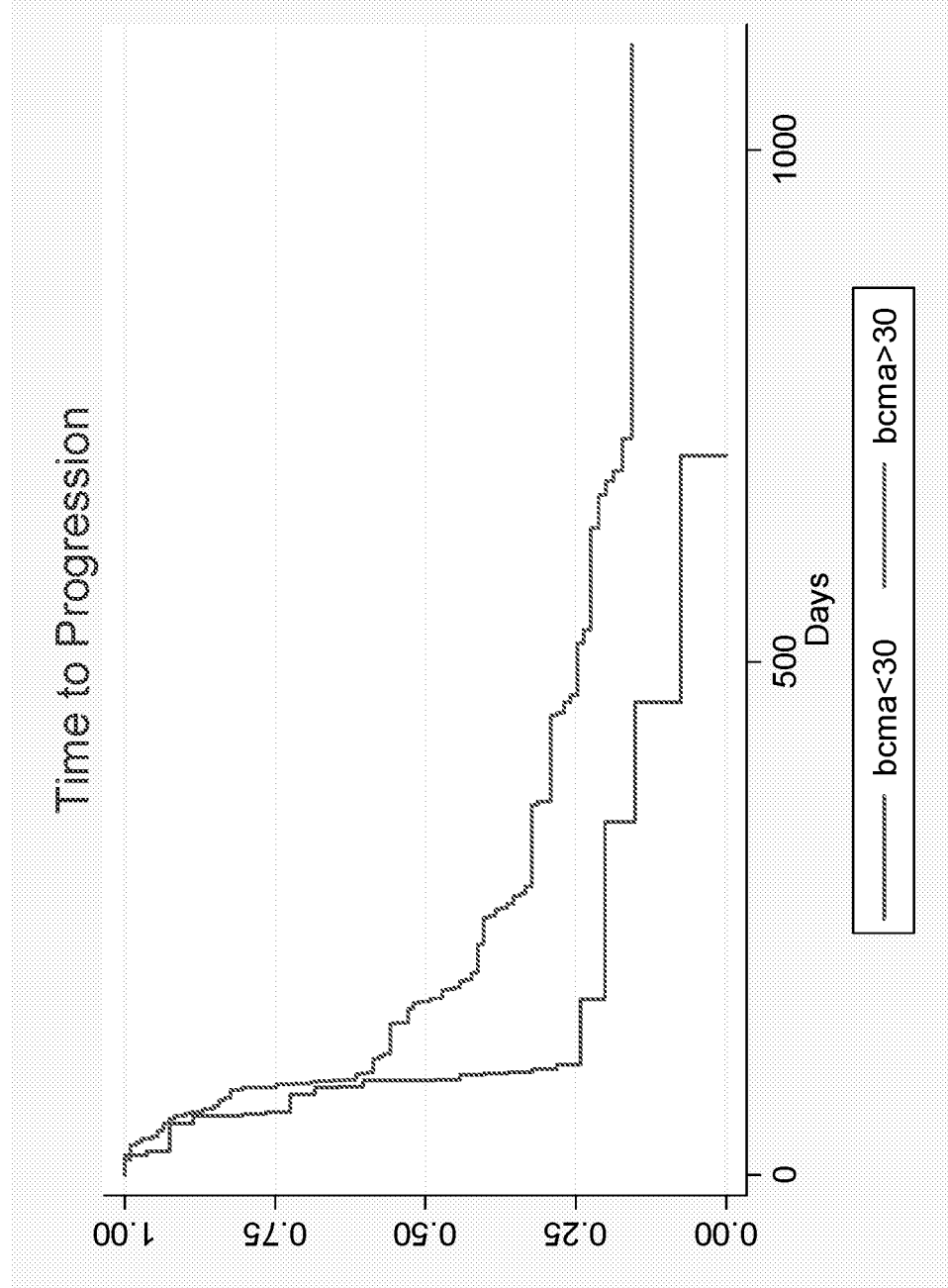
FIG. 1 shows that subjects with serum BCMA polypeptide levels lower than 30 ng/mL have reduced time to progression (TTP) of breast cancer compared to subjects with serum BCMA polypeptide levels higher than 30 ng/mL (but lower than 150 ng/mL). Therefore, serum BCMA polypeptide levels lower than 30 ng/mL correlate with reduced TTP in subjects suffering from breast cancer. Additionally, serum BCMA polypeptide levels lower than 30 ng/mL are predictive of a shorter progress free survival (PFS) in subjects suffering from breast cancer.

The present inventors have found that the levels of BCMA or a fragment thereof in a biological sample correlates with the progression free survival (PFS), overall survival (OS), and time to progression (TTP) to cancer of a subject having or suspected of having a solid tumor type of cancer. Additionally, the levels of BCMA or a fragment thereof in a biological sample correlate with a subject's response to therapy to a solid tumor type of cancer. Therefore, the present inventors have discovered that the levels of BCMA or a fragment thereof in a biological sample of a subject is a reliable diagnostic, prognostic, and treatment monitoring biomarker of solid tumor type of cancers including, without limitation, breast cancer, astrocytoma, head and neck squamous cell cancer, squamous cell carcinoma of head and neck, brain cancer, nervous system cancer, papillary renal cell carcinoma Type II, hepatocellular carcinoma, lung cancer such as small cell lung cancer and non-small cell lung cancer, pancreatic cancer, gall bladder cancer, esophageal cancer, bladder cancer, testicular cancer, ovarian cancer, uterine cancer, colon cancer, rectal cancer, cervical cancer, thyroid cancer, epithelial cancer, esophageal carcinoma, large bowel cancer, neuroblastoma, glioblastoma, glioma, prostate cancer, ovarian cancer, endometrial cancer, stomach cancer, oral cancer, throat cancer, tracheal cancer, bone cancer, liver cancer, sarcoma, skin cancer, squamous cell carcinomas of the mouth, throat, larynx, and lung, and colorectal cancer.

In various embodiments a method of predicting time to progression (TTP) to a solid tumor cancer in a subject, comprising detecting an amount of BCMA polypeptide or a fragment thereof in a biological sample obtained from the subject, wherein an amount of BCMA polypeptide or a fragment thereof in the biological sample of lower than about 30 ng/mL correlates with a reduced time to progression to cancer, wherein the biological sample is a serum sample, or plasma sample, or supernatant obtained from a culture of the subject's bone marrow mononuclear cells or peripheral blood mononuclear cells.

In other embodiments is provided is provided a method of prognosis for progression-free survival (PFS) of a subject having or suspected of having a solid tumor cancer, comprising detecting an amount of BCMA polypeptide or a fragment thereof in a biological sample obtained from the subject, wherein an amount of BCMA polypeptide or a fragment thereof in the biological sample of lower than about 30 ng/mL indicates a reduced length of progression-free survival for the subject, wherein the biological sample is a serum sample, or plasma sample, or supernatant obtained from a culture of the subject's bone marrow mononuclear cells or peripheral blood mononuclear cells.

In additional embodiments is provided a method of prognosis for overall survival (OS) of a subject having or suspected of having a solid tumor cancer, comprising detecting an amount of BCMA polypeptide or a fragment thereof in a biological sample obtained from the subject, wherein an amount of BCMA polypeptide or a fragment thereof in the biological sample of lower than about 15 ng/mL or higher than about 150 ng/mL indicates a reduced overall survival (OS) for the subject, wherein the biological sample is a serum sample, or plasma sample, or supernatant obtained from a culture of the subject's bone marrow mononuclear cells or peripheral blood mononuclear cells.

In other aspects, is provided a method of monitoring progression or response to treatment of a solid tumor type of cancer, comprising detecting an amount of BCMA or a fragment thereof in a biological sample obtained from a subject diagnosed with the cancer at a time point following treatment, wherein an amount of BCMA polypeptide or a fragment thereof in the biological sample of lower than about 30 ng/mL or higher than about 150 ng/mL indicates that the cancer will progress sooner, and wherein an amount of BCMA polypeptide or a fragment thereof in the biological sample of higher than about 30 ng/mL but lower than about 150 ng/mL indicates that the cancer is more likely to enter remission or respond to treatment, wherein the biological sample is a serum sample, or plasma sample, or supernatant obtained from a culture of the subject's bone marrow mononuclear cells or peripheral blood mononuclear cells.

In an embodiment, the amount of BCMA polypeptide or a fragment thereof in the biological sample being lower than about 5 ng/mL, about 10 ng/mL, 15 ng/mL, about 20 ng/mL, 25 ng/mL, about 30 ng/mL, 35 ng/mL, or about 40 ng/mL correlates with a reduced time to progression (TTP) of the cancer.

In an embodiment, the amount of BCMA polypeptide or a fragment thereof in the biological sample being lower than about 5 ng/mL, about 10 ng/mL, 15 ng/mL, about 20 ng/mL, 25 ng/mL, about 30 ng/mL, 35 ng/mL, or about 40 ng/mL indicates a reduced length of progression-free survival (PFS) for the subject.

In an embodiment, the amount of BCMA polypeptide or a fragment thereof in the biological sample being lower than about 5 ng/mL, about 10 ng/mL, 15 ng/mL, about 20 ng/mL, 25 ng/mL, about 30 ng/mL, 35 ng/mL, or about 40 ng/mL indicates a reduced overall survival (OS) for the subject.

In an embodiment, the amount of BCMA polypeptide or a fragment thereof in the biological sample being higher than about 100 ng/mL, about 110 ng/mL, 120 ng/mL, about 130 ng/mL, 140 ng/mL, about 150 ng/mL, 160 ng/mL, or about 170 ng/mL indicates a reduced overall survival (OS) for the subject.

In some embodiments, the solid tumor type of cancer is selected from the group consisting of breast cancer, astrocytoma, head and neck squamous cell cancer, squamous cell carcinoma of head and neck, brain cancer, nervous system cancer, papillary renal cell carcinoma Type II, hepatocellular carcinoma, lung cancer such as small cell lung cancer and non-small cell lung cancer, pancreatic cancer, gall bladder cancer, esophageal cancer, bladder cancer, testicular cancer, ovarian cancer, uterine cancer, colon cancer, rectal cancer, cervical cancer, thyroid cancer, epithelial cancer, esophageal carcinoma, large bowel cancer, neuroblastoma, glioblastoma, glioma, prostate cancer, ovarian cancer, endometrial cancer, stomach cancer, oral cancer, throat cancer, tracheal cancer, bone cancer, liver cancer, sarcoma, skin cancer, squamous cell carcinomas of the mouth, throat, larynx, and lung, and colorectal cancer. In specific aspects, the solid tumor cancer is breast cancer.

In some embodiments, the biological sample includes, without limitation, cells in culture, cell supernatants, cell lysates, serum, plasma, urine, cerebral spinal fluid, biological fluid, and tissue samples. In certain embodiments, the biological sample is a serum sample. In other embodiments, the biological sample is supernatant obtained from culture of the subject's bone marrow mononuclear cells. In yet other embodiments, the biological sample is supernatant obtained from culture of the subject's peripheral blood mononuclear cells.

In some embodiments, the BCMA fragment is a cleaved BCMA polypeptide. In some embodiments, the cleaved BCMA polypeptide is a soluble form of the BCMA polypeptide. The cleaved BCMA polypeptide is provided as SEQ ID NO: 1. The full length BCMA polypeptide is provided as SEQ ID NO: 2. In additional embodiments, BCMA polypeptide or a fragment thereof comprises the amino acid sequence of SEQ ID NO: 1. In yet other embodiments, the BCMA polypeptide or a fragment thereof comprises an amino acid sequence having at least about 90% identity with SEQ ID NO: 1. In still other embodiments, the BCMA polypeptide or a fragment thereof comprises an amino acid sequence having at least about 80% identity with SEQ ID NO: 1. In other aspects, the BCMA polypeptide or a fragment thereof comprises an amino acid sequence having at least about 75% identity with SEQ ID NO: 1.

In additional embodiments, the BCMA polypeptide or a fragment thereof is detected using a detection system selected from the group consisting of: an immunohistochemistry, enzyme-linked immunosorbent assay (ELISA), radioimmunoassay (RIA), enzyme immunoassay (EIA), fluorescence immunoassay (FIA), luminescence immunoassay (LIA), lateral flow assay, or strip assay. In some embodiments, the detection system is a lateral flow assay.

In some embodiments, the detection is performed using an antibody specific for BCMA polypeptide or a fragment thereof. In certain embodiments, the antibody specific for BCMA polypeptide or a fragment thereof is a monoclonal antibody. In other embodiments, the antibody specific for BCMA polypeptide or a fragment thereof is a polyclonal antibody.

In certain embodiments, the amount of BCMA polypeptide or a fragment thereof in the biological sample is lower than about 25 ng/mL. In other embodiments, the amount of BCMA polypeptide or a fragment thereof in the biological sample is lower than about 20 ng/mL.

In some embodiments, a kit for monitoring progression or response to treatment of a solid tumor cancer is provided. In certain aspects, the kit for monitoring progression or response to treatment of a solid tumor cancer comprises a reagent suitable for determining levels of BCMA polypeptide or a fragment thereof in a biological sample obtained from the subject, wherein the biological sample is a serum or plasma sample or supernatant obtained from culture of the subject's bone marrow mononuclear cells or peripheral blood mononuclear cells.

In some embodiments, the kit comprises an antibody specific for BCMA polypeptide or fragment thereof. In certain embodiments, the antibody specific for BCMA polypeptide or fragment thereof is a polyclonal antibody. In other embodiments, the antibody specific for BCMA polypeptide or fragment thereof is a monoclonal antibody.

In some aspects, the kit comprises a detection system selected from the group consisting of: ELISA assay, RIA assay, EIA assay, FIA assay, LIA assay, lateral flow assay, or strip assay.

In various embodiments, methods for reliably monitoring the likelihood of survival of a subject having a solid tumor cancer are provided. The present inventors have surprisingly found that levels of BCMA or a fragment thereof in a biological sample (e.g., a subject's sera) can be used for prognosis purposes, in determining the likelihood of progress free survival (PFS) and/or overall survival (OS) of a subject having or suspected of having a solid tumor type of cancer. In other embodiments, methods for reliably predicting time to progression (TTP) to a solid tumor type of cancer in a subject having a solid tumor type of cancer are provided. The present inventors have surprisingly found that levels of BCMA or a fragment thereof in a biological sample (e.g., a subject's sera) can be used to reliably predict time to progression to a solid tumor cancer in a subject having or suspected of having a solid tumor type of cancer. The present inventors have previously shown that BCMA levels correlate with the immune status of a subject. Thus, without wishing to be bound to a particular theory, it is believed that because levels of BCMA or a fragment thereof in a biological sample obtained from a subject correlate with the immune status of the subject, the levels of BCMA or a fragment thereof in the biological sample can be determined and be used for prognostic purposes, in determining the likelihood of survival of a subject having a solid tumor type of cancer.

In various embodiments, methods for reliably monitoring progression of a solid tumor type of cancer or response to treatment of a solid tumor type of cancer of a subject are provided. The present inventors have surprisingly found that levels of BCMA or a fragment thereof in a biological sample (e.g., a subject's sera) can be detected to reliably monitor progression of cancer or response to treatment of cancer of a subject. Without wishing to be bound to a particular theory, it is believed that because levels of BCMA or a fragment thereof in a biological sample obtained from a subject correlate with the immune status of the subject, the levels of BCMA or a fragment thereof in the biological sample can be determined at different times point subsequent to start of the treatment and compared to an initial time point prior to start of the treatment to monitor the response of a subject to treatments targeted to improve the immune status of the subject.

In certain embodiments, the reduced PFS, reduced TTP, and/or reduced OS is a result of an impaired immune system in the subjects having or suspected of having a solid tumor type of cancer, as indicated by the lower levels of BCMA polypeptide or a fragment thereof in a biological sample (e.g., serum or plasma).

The practice of the invention will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., *Molecular Cloning: A Laboratory Manual* (3rd Edition, 2001); Sambrook, et al., *Molecular Cloning: A Laboratory Manual* (2nd Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford, 1985); Anand, *Techniques for the Analysis of Complex Genomes*, (Academic Press, New York, 1992); *Transcription and Translation* (B. Hames & S. Higgins, Eds., 1984); Perbal, *A Practical Guide to Molecular Cloning* (1984); and Harlow and Lane, *Antibodies*, (Cold Spring Harbor Laboratory Press, Cold Spring Harbor, N.Y., 1998).

All publications, patents and patent applications cited herein are hereby incorporated by reference in their entirety.

A. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred embodiments of compositions, methods and materials are described herein. For the purposes of the present invention, the following terms are defined below.

The articles "a," "an," and "the" are used herein to refer to one or to more than one (i.e., to at least one) of the grammatical object of the article. By way of example, "an element" means one element or more than one element.

As used herein, the term "about" or "approximately" refers to a quantity, level, value, number, frequency, percentage, dimension, size, amount, weight or length that varies by as much as 30, 25, 20, 25, 10, 9, 8, 7, 6, 5, 4, 3, 2, or 1% to a reference quantity, level, value, number, frequency, percentage, dimension, size, amount, weight or length. In particular embodiments, the terms "about" or "approximately" when preceding a numerical value indicates the value plus or minus a range of 15%, 10%, 5%, or 1%.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Reference throughout this specification to "one embodiment," "an embodiment," "embodiment," "a particular embodiment," "a related embodiment," "a certain embodiment," "an additional embodiment," "some embodiments," "other embodiments," "additional embodiments," "Further embodiments," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "BCMA" is intended to generically refer to both the wild-type and variant B-cell maturation antigen polypeptides, unless specifically denoted otherwise. BCMA polypeptides are encoded by the BCMA gene. As it is commonly used in the art, the term "gene" is intended to refer to the genomic region encompassing 5' untranslated region(s) (UTR), exons, introns, and 3' UTR. Individual segments may be specifically referred to, e.g., promoter, coding region, etc. Combinations of such segments that provide for a complete BCMA protein may be referred to generically as a protein coding sequence. There are four major haplotypes of the BCMA gene in the human genome, in the present disclosure the term "BCMA" is meant to encompass all four (Kawasaki et al., *Genes Immun.* 2: 276-9, 2001).

The terms "BCMA" or "BCMA polypeptide" are used interchangeably and encompass an amino acid sequence encoded by an open reading frame (ORF) of a known BCMA polynucleotide, including the full-length native polypeptide and fragments thereof, particularly biologically active fragments and/or fragments corresponding to functional domains, e.g., a region or domain having biological activity, etc.; antigenic fragments thereof, and including fusions of the subject polypeptides to other proteins or parts thereof. The amino acid sequences of BCMA polypeptides have been disclosed. (See e.g., Laabi et al., *Nucleic Acids Research* 22: 1147-1154, 1994; Laabi et al., *EMBO* 1, 11: 3897-3904 (1992); Gras et al., *Int. Immunology*, 7: 1093-1106 (1995); and Madry et al., *Int. Immunology*, 10: 1693-1702 (1998). The BCMA polypeptides of the invention can be isolated from a variety of sources, such as from human tissue types or biological samples such as serum, plasma, bone, marrow, or tissue.

As used herein, the term "fragment thereof" refers to a portion of the full-length native BCMA polypeptide. In some embodiments, the BCMA fragment is a cleaved BCMA polypeptide. In some embodiments, the cleaved BCMA polypeptide is a soluble form of the BCMA polypeptide. In some embodiments, the BCMA polypeptide or a fragment thereof comprises an amino acid sequence having at least about 20% identity, at least about 30% identity, at least about 40% identity, at least about 50% identity, at least about 60% identity, at least about 70% identity, at least about 75% identity, at least about 80% identity, at least about 90% identity, at least about 95% identity, at least about 96% identity, at least about 97% identity, at least about 98% identity, or at least about 99% identity with the full-length native BCMA polypeptide.

As used herein, the term "immune status" of a subject refers to the efficiency of the subject's immune system. As such, the immune status of a subject indicates whether the subject's immune system is normal, impaired (for e.g., if the subject is afflicted with an immune deficiency disease), or hyperactive (for e.g., if the subject is afflicted with a disease, an autoimmune disease, or an illness) compared to a normal healthy subject.

The term "immune system" refers to a system of many biological structures and processes within an organism that protects against disease.

The following are non-limiting embodiments of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A nucleic acid molecule may also comprise modified nucleic acid molecules, such as methylated nucleic acid molecules and nucleic acid molecule analogs. Analogs of purines and pyrimidines are known in the art. Nucleic acids may be naturally occurring, e.g., DNA or RNA, or may be synthetic analogs, as known in the art. Such analogs may be preferred for use as probes because of superior stability under assay conditions. Modifications in the native structure, including alterations in the backbone, sugars or heterocyclic bases, have been shown to increase intracellular stability and binding affinity. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. In various embodiments, BCMA polypeptides are contemplated for use within diagnostic, prognostic, or monitoring compositions and methods disclosed herein. The term includes fusion proteins, including, but not limited to, fusion proteins with a heterologous amino acid sequence, fusions with heterologous and homologous leader sequences, with or without N-terminal methionine residues; immunologically tagged proteins; and the like.

A "substantially isolated" or "isolated" substance is one that is substantially free of its associated surrounding materials in nature. By substantially free is meant at least 50%, preferably at least 70%, more preferably at least 80%, and even more preferably at least 90% free of the materials with which it is associated in nature. As used herein, an "isolated" can refer to polynucleotides, polypeptides, cells, samples, and antibodies.

Hybridization reactions can be performed under conditions of different "stringency". Conditions that increase stringency of a hybridization reaction are widely known and published in the art. See, for example, Sambrook et al. (1989). Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water. Examples of stringent conditions are hybridization and washing at 50° C. or higher and in 0.1×SSC (9 mM NaCl/0.9 mM sodium citrate).

The term "target cell" includes an individual cell, cell from a biological sample, or cell culture. Target cells include progeny of a single target cell, and the progeny may not necessarily be completely identical (in morphology or in total DNA complement) to the original parent cell due to natural, accidental, or deliberate mutation and/or change. In particular embodiments, target cells include multiple myeloma, chronic lymphocytic leukemia, lymphoma, or Waldenstrom's macroglobulinemia tumor cells, bone marrow or peripheral blood mononuclear cells, B-cells, or plasma cells.

The detection systems of the invention are based, in part, on the ability of a binding agent to bind BCMA or a fragment thereof. Generally, the invention contemplates the use of a binding agent that specifically binds BCMA or a fragment thereof, resulting in the formation of a detectable complex of BCMA or a fragment thereof and binding agent. In some embodiments, the invention utilizes two binding agents, a capture binding agent and a detection binding agent, both of which bind to BCMA or a fragment thereof, resulting in the formation of a ternary complex comprising capture binding agent, BCMA, and detection binding agent.

Any of a variety of binding agents may be used, including, for example, polypeptides, sugars, and nucleic acids. In yet other embodiments, the invention further includes the use of an additional binding agent that binds to the detection binding agent. Such an additional binding agent may be useful, e.g., in detecting bound detection binding agent. Accordingly, one example of such an additional binding agent is antibodies specific for a fragment of an antibody, e.g., an $F_c$ fragment, which may be detectably labeled and, therefore used to detect bound detection binding agent, and are particularly useful when the detection binding agent is not itself easily amenable to labeling. In certain embodiments, the binding agent is an antibody specific for bacteria.

The term "binds specifically," in the context of antibody binding, refers to high avidity and/or high affinity binding of an antibody to a specific polypeptide i.e., epitope of a BCMA or a fragment thereof. Antibody binding to an epitope on a specific polypeptide (also referred to herein as "an epitope") is preferably stronger than binding of the same antibody to any other epitope, particularly those which may be present in molecules in association with, or in the same sample, as the specific polypeptide of interest, e.g., binds more strongly to a specific BCMA epitope than to a different BCMA epitope or non-BCMA epitope. Antibodies which bind specifically to a polypeptide of interest may be capable of binding other polypeptides at a weak, yet detectable, level (e.g., 10% or less, 5% or less, 1% or less of the binding shown to the polypeptide of interest). Such weak binding, or background binding, is readily discernible from the specific antibody binding to the compound or polypeptide of interest, e.g. by use of appropriate controls. In general, antibodies used in compositions and methods of the invention which bind to a specific BCMA polypeptide or a fragment thereof with a binding affinity of $10^7$ moles/L or more, preferably $10^8$ moles/L or more are said to bind specifically to the specific BCMA polypeptide. In general, an antibody with a binding affinity of $10^6$ moles/L or less is not useful in that it will not bind an antigen at a detectable level using conventional methodology currently used.

In some embodiments, the affinity of specific binding of a BCMA binding agent to BCMA or a fragment thereof is about 2 times greater than background binding, about 5 times greater than background binding, about 10 times greater than background binding, about 20 times greater than background binding, about 50 times greater than background binding, about 100 times greater than background binding, or about 1000 times greater than background binding or more.

In other embodiments, the affinity of specific binding is between about 2 to about 1,000 times greater than background binding, between about 2 to 500 times greater than background binding, between about 2 to about 100 times greater than background binding, between about 2 to about 50 times greater than background binding, between about 2 to about 20 times greater than background binding, between about 2 to about 10 times greater than background binding, between about 5 to about 100 times greater than background binding, between about 5 to about 50 times greater than background binding, between about 5 to about 20 times greater than background binding, between about 10 to about 100 times greater than background binding, between about 10 to about 50 times greater than background binding, between about 50 to about 500 times greater than background binding, or any intervening range of affinity.

Accordingly, specific binding occurs between a binding agent and BCMA or a fragment thereof where there is an interaction between the two which produces a bound complex having the characteristics of an antibody/antigen or enzyme/substrate interaction. In some embodiments, specific binding is characterized when one member of a pair substantially binds to a particular species and to no other species within the family of compounds to which the corresponding member of the binding member belongs. In other embodiments, specific binding is characterized when one member of a pair substantially binds to one or more particular species and to no other species within the family of compounds to which the corresponding member of the binding member belongs. In yet other embodiments, specific binding is characterized when one member of a pair substantially binds to 1, 2, 3, 4, 5, 6, 7, 8, 9, 10, or more particular species and to no other species within the family of compounds to which the corresponding member of the binding member belongs.

Generally speaking, the binding affinity of a binding agent of the invention (A) to BCMA or a fragment thereof (B) can be generally expressed by the chemical equilibrium constant $K_d$ resulting from the following reaction: [A]+[B]−[AB]. The chemical equilibrium constant $K_d$ is then given by:

$K_d=[A]\times[B]/[AB]$. Whether the binding of a binding agent is specific or not can be judged from the difference between the binding affinity ($K_d$ value) of the binding agent to BCMA or a fragment thereof, versus the binding to another polypeptide.

$K_d$ values and differences in $K_d$ values can be measured using, for example, in vitro or in vivo binding assays and/or assays on other materials such as a polystyrene microtitre plate or a specialized surface in an analytical biosensor. In some embodiments, the difference between the $K_d$ value of a binding agent to BCMA or a fragment thereof, versus the binding to an undesired polypeptide is about 2-fold, about 3-fold, about 4-fold, about 5-fold, about 6-fold, about 7-fold, about 8-fold, about-9 fold, about 10-fold, about 20-fold, about 50-fold, about 100-fold, about 1000-fold, or more.

In other embodiments, the $K_d$ value is less than $10^4$ M, less than $10^5$ M, less than $10^6$ M, less than $10^7$ M, less than $10^8$ M, less than $10^9$ M, less than $10^{10}$ M and could be $10^{11}$ M, less than $10^{12}$ M, less than $10^{13}$ M, less than $10^{14}$ M, less than $10^{15}$ M or less.

In other aspects, the $K_d$ value is between about $10^4$ M and about $10^{15}$ M, between about $10^4$ M and about $10^{12}$ M, between about $10^4$ M and about $10^{10}$ M, between about $10^6$ M and about $10^{15}$ M, between about $10^6$ M and about $10^{12}$ M, between about $10^6$ M and about $10^{10}$ M, between about $10^8$ M and about $10^{15}$ M, between about $10^8$ M and about $10^{12}$ M, between about $10^8$ M and about $10^{10}$ M, between about $10^7$ M and about $10^{10}$ M, or any intervening range of affinity.

The term "antibody" herein is used in the broadest sense and specifically covers monoclonal antibodies, polyclonal antibodies, multispecific antibodies (e.g., bispecific antibodies) formed from at least two intact antibodies, and antibody fragments so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that can be present in minor amounts.

In some embodiments, the monoclonal antibody is an anti-BCMA monoclonal antibody. In other embodiments, the monoclonal antibody specifically recognizes an epitope present in a fragment of the BCMA polypeptide.

Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256: 495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352: 624-628 (1991) and Marks et al., J. Mol. Biol., 222: 581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain (s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81: 6851-6855 (1984)). Methods of making chimeric antibodies are known in the art.

"Humanized" forms of non-human (e.g., murine) antibodies are chimeric immunoglobulins, immunoglobulin chains or fragments thereof (such as Fv, Fab, Fab', F (ab') 2 or other antigen-binding subsequences of antibodies) which contain minimal sequence derived from non-human immunoglobulin.

For the most part, humanized antibodies are human immunoglobulins (recipient antibody) in which residues from a complementarity-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence although the FR regions may include one or more amino acid substitutions that improve binding affinity. The number of these amino acid substitutions in the FR is typically no more than 6 in the H chain, and no more than 3 in the L chain. The humanized antibody optimally also will comprise at least a portion of an immunoglobulin constant region (Fc), typically that of a human immunoglobulin. For further details, see Jones et al., Nature, 321: 522-525 (1986); Reichmann et al., Nature, 332: 323-329 (1988); and Presta, Curr. Op. Struct. Biol., 2: 593-596 (1992). The humanized antibody includes a PRIMATIZED antibody wherein the antigen-binding region of the antibody is derived from an antibody produced by, e.g., immunizing macaque monkeys with the antigen of interest. Methods of making humanized antibodies are known in the art.

Human antibodies can also be produced using various techniques known in the art, including phage-display libraries. Hoogenboom and Winter, J. Mol. Biol., 227: 381 (1991); Marks et al., J. Mol. Biol., 222: 581 (1991). The techniques of Cole et al. and Boerner et al. are also available for the preparation of human monoclonal antibodies. Cole et al., Monoclonal Antibodies and Cancer Therapy, Alan R. Liss, p. 77 (1985); Boerner et al., J. Immunol., 147(1): 86-95 (1991).

"Functional fragments" of the binding antibodies of the invention are those fragments that retain binding to antigen with substantially the same affinity as the intact full chain molecule from which they are derived.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than about 95% by weight of antibody as determined by the Lowry method, and most preferably more than about 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The terms "detectably labeled antibody" refers to an antibody (or antibody fragment which retains binding specificity for a BCMA or a fragment thereof), having an attached detectable label. The detectable label is normally attached by-chemical conjugation, but where the label is a polypeptide, it could alternatively be attached by genetic engineering techniques. Methods for production of detectably labeled proteins are well known in the art. Detectable labels may be selected from a variety of such labels known in the art, including, but not limited to, haptens, radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin)), methods for labeling antibodies, and methods for using labeled antibodies are well known in the art (see, for example, Harlow and Lane, eds. (*Antibodies: A Laboratory Manual* (1988) Cold Spring Harbor Laboratory Press, Cold Spring Harbor, N.Y.)).

In one technique, an immunogen comprising the polypeptide is initially injected into any of a wide variety of mammals (e.g., mice, rats, rabbits, sheep or goats). Polyclonal antibodies specific for the polypeptide may then be purified from such antisera by, for example, affinity chromatography using the polypeptide coupled to a suitable solid support. In some embodiments, the antibody is an anti-BCMA polyclonal antibody. In other embodiments, the antibody is polyclonal antibody that recognizes a fragment of the BCMA polypeptide.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived there from and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes, without limitation, cells in culture, cell supernatants, cell lysates, serum, plasma, urine, cerebral spinal fluid, biological fluid, and tissue samples. The sample may be pretreated as necessary by dilution in an appropriate buffer solution or concentrated, if desired. Any of a number of standard aqueous buffer solutions, employing one of a variety of buffers, such as phosphate, Tris, or the like, preferably at physiological pH can be used. Biological samples can be derived from patients using well known techniques such as venipuncture, lumbar puncture, fluid sample such as saliva or urine, or tissue biopsy and the like.

As used herein, the terms "correlated with" or "associated with" refer to the levels of BCMA or a fragment thereof in a biological sample of a subject that has a statistically significant correlation with a physiologic state, e.g., disease status or extent of the disease, response to treatment, and survival. The strength of the correlation between levels of BCMA or a fragment thereof and the presence or absence of a particular physiologic state may be determined by a statistical test of significance. Methods for determining the strength of a correlation between the expression level of a differentially-expressed gene and a particular physiologic state by assigning a statistical score to the correlation are reviewed in Holloway et al. (2002) *Nature Genetics* Suppl. 32: 481-89, Churchill (2002) *Nature Genetics* Suppl. 32: 490-95, Quackenbush (2002) *Nature Genetics* Suppl. 32: 496-501; Slonim (2002) *Nature Genetics* Suppl. 32: 502-08; and Chuaqui et al. (2002) *Nature Genetics* Suppl. 32: 509-514; each of which is herein incorporated by reference in its entirety.

A "conjugate" refers to any molecule, e.g., antibody bound or joined covalently or non-covalently to another molecule, e.g., a hapten, small molecule, or label, including fusion proteins and as well as molecules that contain both amino acid or protein portions and non-protein portions. Conjugates may be synthesized by a variety of techniques known in the art including, for example, solid phase synthesis, solution phase synthesis, organic chemical synthetic techniques or a combination of these techniques. The choice of synthesis will depend upon the particular molecule to be generated.

The terms "individual," "subject," and "patient," used interchangeably herein, refer to a mammal, including, but not limited to, murines, simians, humans, mammalian farm animals, mammalian sport animals, and mammalian pets. In some embodiments, the subject is a human subject.

The term "mammal" refers to any animal classified as a mammal, including humans, domestic and farm animals, and zoo, sports, or pet animals, such as dogs, horses, cats, cows, etc. In some embodiments, the mammal herein is human.

B. Methods of Diagnosis, Prognosis and Monitoring of Solid Tumor Cancers

The present inventors have surprisingly discovered that BCMA polypeptide levels or levels of a fragment thereof in a biological sample can be reliably used as prognosis for progression-free survival and/or overall survival of a subject having or suspected of having a solid tumor type of cancer. In addition, BCMA polypeptide levels or levels of a fragment thereof in a biological sample can be reliably used to predict time to progression to a solid tumor type of cancer in a subject.

Furthermore, the present inventors have surprisingly found that that BCMA polypeptide levels or levels of a fragment thereof in a biological sample can be reliably used for reliably monitoring progression of a solid tumor cancer or response to treatment of a solid tumor type of cancer of a subject.

In some embodiments, the solid tumor type of cancer includes, without limitation, breast cancer, astrocytoma, head and neck squamous cell cancer, squamous cell carcinoma of head and neck, brain cancer, nervous system cancer, papillary renal cell carcinoma Type II, hepatocellular carcinoma, lung cancer such as small cell lung cancer and non-small cell lung cancer, pancreatic cancer, gall bladder cancer, esophageal cancer, bladder cancer, testicular cancer, ovarian cancer, uterine cancer, colon cancer, rectal cancer, cervical cancer, thyroid cancer, epithelial cancer, esophageal carcinoma, large bowel cancer, neuroblastoma, glioblastoma, glioma, prostate cancer, ovarian cancer, endometrial cancer, stomach cancer, oral cancer, throat cancer, tracheal cancer, bone cancer, liver cancer, sarcoma, skin cancer, squamous cell carcinomas of the mouth, throat, larynx, and lung, and colorectal cancer. In specific aspects, the solid tumor type of cancer is breast cancer.

Accordingly, particular embodiments of the invention provide methods of diagnosis of solid tumor type of cancers in subjects, prognosis of survival in subjects diagnosed with solid tumor type of cancers as well as monitoring the response of the disease to treatment, based upon the level of BCMA polypeptide or a fragment thereof in a biological sample obtained from a subject, including, e.g., a subject's bloodstream, serum, bone marrow, or tissue. In various embodiments, the biological sample includes, without limitation, cells in culture, cell supernatants, cell lysates, bloodstream, serum, plasma, urine, cerebral spinal fluid, biological fluid, and tissue samples. In certain embodiments, the biological sample is supernatant obtained from a culture of the subject's cells. In some aspects, the cells are the subject's bone marrow mononuclear cells. In other aspects, the cells are the subject's peripheral blood mononuclear cells.

In some embodiments, the BCMA polypeptide of the invention is a soluble BCMA polypeptide. In certain embodiments, the soluble BCMA polypeptide comprises the extracellular domain of a full-length BCMA polypeptide. In other embodiments, the soluble BCMA polypeptide comprises a fragment of the extracellular domain of a full-length BCMA polypeptide. In certain aspects, the BCMA fragment is a cleaved BCMA polypeptide.

In some embodiments, the BCMA polypeptide or a fragment thereof comprises the amino acid sequence of SEQ ID NO: 1. In other embodiments, the BCMA polypeptide or a fragment thereof comprises an amino acid sequence having at least about 20%, at least about 25%, at least about 30%, at least about 35%, at least about 40%, at least about 85%, at least about 50%, at least about 55%, at least about 60%, at least about 65%, at least about 70%, at least about 75%, at least about 80%, at least about 85%, at least about 90%, at least about 95%, at least about 96%, at least about 98%, or at least about 99% identity with SEQ ID NO: 1. In certain aspects, the BCMA polypeptide or a fragment thereof comprises an amino acid sequence having at least about 90% identity with SEQ ID NO: 1. In other aspects, the BCMA polypeptide or a fragment thereof comprises an amino acid sequence having at least about 80% identity with SEQ ID NO: 1. In yet other aspects, the BCMA polypeptide or a fragment thereof comprises an amino acid sequence having at least about 75% identity with SEQ ID NO: 1.

A variety of methods of determining BCMA levels are known and available in the art. In certain embodiments, these involve the use of a BCMA binding agent, such as a BCMA specific antibody. As discussed elsewhere herein, there are a variety of assay formats known to those of ordinary skill in the art and suitable for using a binding agent to detect polypeptide markers in a sample. E.g., ELISA assays, lateral flow assays, etc.; see also, Harlow and Lane, *Antibodies: A Laboratory Manual*, Cold Spring Harbor Laboratory, 1988.

In particular embodiments, detection involves measuring BCMA mRNA levels present in the biological sample. In other embodiments, detection involves determining BCMA polypeptide levels present in the biological sample. In some embodiments, detection is performed using one or more primers specific for BCMA. In other embodiments, detection is performed using an antibody specific for BCMA or a fragment thereof.

In certain embodiments, the diagnosis, prognosis, or monitoring of solid tumor cancers involves determining the absolute amount of a BCMA polypeptide or a fragment thereof in a biological sample of a subject. Thus, in some embodiments, a method of prognosis for the PFS of a subject having or suspected of having a solid tumor type of cancer is provided.

In certain embodiments, the levels of serum BCMA polypeptide levels or a fragment thereof in patients suffering from a solid tumor cancer is lower than about 30 ng/mL, lower than about 25 ng/mL, lower than about 20 mg/mL, lower than about 15 mg/mL, lower than about 10 mg/mL, or lower than about 5 mg/mL. In certain aspects, an amount of BCMA polypeptide or a fragment thereof in a biological sample of the subject of lower than about 30 ng/mL indicates a reduced chance of PFS for the subject. In other aspects, the amount of BCMA polypeptide or a fragment thereof in the biological sample is lower than about 25 ng/mL. In yet other aspects, the amount of BCMA polypeptide or a fragment thereof in the biological sample is lower than about 20 ng/mL.

In certain embodiments, subjects with BCMA polypeptide levels lower than about 30 ng/mL in a biological sample have reduced PFS to a solid tumor type of cancer compared to subjects with BCMA polypeptide levels higher than about 30 ng/mL. In other embodiments, subjects with BCMA polypeptide levels lower than about 30 ng/mL in a biological sample have reduced PFS to a solid tumor cancer compared to subjects with BCMA polypeptide levels higher than about 30 ng/mL, but lower than about 150 ng/mL. Therefore, in certain aspects, BCMA polypeptide levels lower than about 30 ng/mL correlate with reduced chance of PFS in subjects having or suspected of having a solid tumor type of cancer. In other aspects, BCMA polypeptide levels higher than about 30 ng/mL but lower than about 150 ng/mL correlate with an increased chance of PFS in subjects having or suspected of having a solid tumor type of cancer.

In certain embodiments, subjects with BCMA polypeptide levels lower than about 25 ng/mL in a biological sample have reduced PFS to a solid tumor type of cancer compared to subjects with BCMA polypeptide levels higher than about 25 ng/mL. In other embodiments, subjects with BCMA polypeptide levels lower than about 25 ng/mL in a biological sample have reduced PFS to a solid tumor type of cancer compared to subjects with BCMA polypeptide levels higher than about 25 ng/mL, but lower than about 150 ng/mL. Therefore, in certain aspects, BCMA polypeptide levels lower than about 25 ng/mL correlate with reduced chance of PFS in subjects having or suspected of having a solid tumor type of cancer. In other aspects, BCMA polypeptide levels higher than about 30 ng/mL but lower than about 150 ng/mL correlate with an increased chance of PFS in subjects having or suspected of having a solid tumor type of cancer.

In certain embodiments, subjects with BCMA polypeptide levels lower than about 20 ng/mL in a biological sample have reduced PFS to a solid tumor type of cancer compared to subjects with BCMA polypeptide levels higher than about 20 ng/mL. In other embodiments, subjects with BCMA polypeptide levels lower than about 20 ng/mL in a biological sample have reduced PFS to a solid tumor type of cancer compared to subjects with BCMA polypeptide levels higher than about 20 ng/mL, but lower than about 150 ng/mL. Therefore, in certain aspects, BCMA polypeptide levels lower than about 20 ng/mL correlate with reduced chance of PFS in subjects having or suspected of having a solid tumor type of cancer. In other aspects, BCMA polypeptide levels higher than about 20 ng/mL but lower than about 150 ng/mL correlate with an increased chance of PFS in subjects having or suspected of having a solid tumor type of cancer.

In some embodiments is included a method of prognosis for PFS of a subject having or suspected of having a solid tumor cancer comprises detecting an amount of BCMA polypeptide or a fragment thereof in a biological sample obtained from the subject, wherein an amount of BCMA polypeptide or a fragment thereof in the biological sample of lower than about 30 ng/mL indicates a reduced chance of PFS for the subject, wherein the biological sample is a serum sample, or plasma sample, or supernatant obtained from a culture of the subject's bone marrow mononuclear cells or peripheral blood mononuclear cells.

In some embodiments, a method of prognosis predicting TTP to a solid tumor type of cancer in a subject is provided. In certain embodiments, the levels of serum BCMA polypeptide levels or a fragment thereof in patients suffering from a solid tumor type of cancer is lower than about 30 ng/mL, lower than about 25 ng/mL, lower than about 20 mg/mL, lower than about 15 mg/mL, lower than about 10 mg/mL, or lower than about 5 mg/mL. In certain aspects, an amount of BCMA polypeptide or a fragment thereof in a biological sample of the subject of lower than about 30 ng/mL correlates with a reduced TTP of the cancer. In other aspects, the amount of BCMA polypeptide or a fragment thereof in the biological sample is lower than about 25 ng/mL. In yet other aspects, the amount of BCMA polypeptide or a fragment thereof in the biological sample is lower than about 20 ng/mL.

In certain embodiments is included a method of predicting TTP to a solid tumor type of cancer in a subject comprises detecting an amount of BCMA polypeptide or a fragment thereof in a biological sample obtained from the subject, wherein an amount of BCMA polypeptide or a fragment thereof in the biological sample of lower than about 30 ng/mL correlates with a reduced time to progression to cancer, wherein the biological sample is a serum sample, or plasma sample, or supernatant obtained from a culture of the subject's bone marrow mononuclear cells or peripheral blood mononuclear cells.

In certain embodiments, subjects with BCMA polypeptide levels lower than about 30 ng/mL in a biological sample have reduced TTP of a solid tumor type of cancer compared to subjects with BCMA polypeptide levels higher than about 30 ng/mL. In other embodiments, subjects with BCMA polypeptide levels lower than about 30 ng/mL in a biological sample have reduced TTP to a solid tumor cancer compared to subjects with BCMA polypeptide levels higher than about 30 ng/mL, but lower than 150 ng/mL. Therefore, in certain aspects, BCMA polypeptide levels lower than about 30 ng/mL correlate with reduced TTP in subjects having or suspected of having a solid tumor type of cancer. In other aspects, BCMA polypeptide levels higher than about 30 ng/mL but lower than about 150 ng/mL correlate with an increased TTP in subjects having or suspected of having a solid tumor type of cancer.

In certain embodiments, subjects with BCMA polypeptide levels lower than about 25 ng/mL in a biological sample have reduced TTP to a solid tumor type of cancer compared to subjects with BCMA polypeptide levels higher than about 25 ng/mL. In other embodiments, subjects with BCMA polypeptide levels lower than about 25 ng/mL in a biological sample have reduced TTP to a solid tumor type of cancer compared to subjects with BCMA polypeptide levels higher than about 25 ng/mL, but lower than 150 ng/mL. Therefore, in certain aspects, BCMA polypeptide levels lower than about 25 ng/mL correlate with reduced TTP in subjects having or suspected of having a solid tumor type of cancer. In other aspects, BCMA polypeptide levels higher than about 25 ng/mL but lower than about 150 ng/mL correlate with an increased TTP in subjects having or suspected of having a solid tumor type of cancer.

In other embodiments, subjects with BCMA polypeptide levels lower than about 20 ng/mL in a biological sample have reduced TTP to a solid tumor type of cancer compared to subjects with BCMA polypeptide levels higher than about 20 ng/mL. In other embodiments, subjects with BCMA polypeptide levels lower than about 20 ng/mL in a biological sample have reduced TTP to a solid tumor type of cancer compared to subjects with BCMA polypeptide levels higher than about 20 ng/mL, but lower than 150 ng/mL. Therefore, in certain aspects, BCMA polypeptide levels lower than about 20 ng/mL correlate with reduced TTP in subjects having or suspected of having a solid tumor type of cancer. In other aspects, BCMA polypeptide levels higher than about 20 ng/mL but lower than about 150 ng/mL correlate with an increased TTP in subjects having or suspected of having a solid tumor type of cancer.

In some embodiments, a method of prognosis for the OS of a subject having or suspected of having a solid tumor type of cancer is provided. In certain embodiments, the levels of serum BCMA polypeptide levels or a fragment thereof in patients suffering from a solid tumor type of cancer is lower than about 15 mg/mL, lower than about 10 mg/mL, or lower than about 5 mg/mL. In certain aspects, an amount of BCMA polypeptide or a fragment thereof in the biological sample of lower than about 15 ng/mL indicates a reduced overall survival (OS) for the subject. In other aspects, an amount of BCMA polypeptide or a fragment thereof in the biological sample of higher than about 150 ng/mL indicates a reduced overall survival (OS) for the subject. In yet other aspects, an amount of BCMA polypeptide or a fragment thereof in the biological sample of lower than about 15 ng/mL or higher than about 150 ng/mL indicates a reduced overall survival (OS) for the subject.

In some embodiments is included a method of prognosis for OS of a subject having or suspected of having a solid tumor type of cancer comprises detecting an amount of BCMA polypeptide or a fragment thereof in a biological sample obtained from the subject, wherein an amount of BCMA polypeptide or a fragment thereof in the biological sample of lower than about 15 ng/mL or higher than about 150 ng/mL indicates a reduced overall survival (OS) for the subject, wherein the biological sample is a serum sample, or plasma sample, or supernatant obtained from a culture of the subject's bone marrow mononuclear cells or peripheral blood mononuclear cells.

In certain embodiments, subjects with BCMA polypeptide levels lower than about 15 ng/mL in a biological sample have reduced OS to a solid tumor type of cancer compared to subjects with BCMA polypeptide levels higher than about 15 ng/mL. In other embodiments, subjects with BCMA polypeptide levels lower than about 15 ng/mL in a biological sample have reduced OS to a solid tumor type of cancer compared to subjects with BCMA polypeptide levels higher than about 15 ng/mL but lower than 150 ng/mL. Therefore, in certain aspects, BCMA polypeptide levels lower than about 15 ng/mL correlate with reduced OS in subjects having or suspected of having a solid tumor type of cancer. In other aspects, BCMA polypeptide levels higher than about 15 ng/mL but lower than about 150 ng/mL correlate with an increased OS in subjects having or suspected of having a solid tumor type of cancer.

In certain embodiments, subjects with BCMA polypeptide levels higher than about 150 ng/mL in a biological sample have reduced OS to a solid tumor type of cancer compared to subjects with BCMA polypeptide levels lower than about 150 ng/mL. In other embodiments, subjects with BCMA polypeptide levels higher than about 150 ng/mL in a biological sample have reduced OS to a solid tumor cancer compared to subjects with BCMA polypeptide levels lower than about 150 ng/mL, but higher than about 30 ng/mL. Therefore, in certain aspects, BCMA polypeptide levels higher than about 150 ng/mL correlate with reduced OS in subjects having or suspected of having a solid tumor type of cancer. In other aspects, BCMA polypeptide levels lower than about 150 ng/mL but higher than about 30 ng/mL correlate with increased OS in subjects having or suspected of having a solid tumor type of cancer.

In some embodiments, a method of monitoring progression or response to treatment of solid tumor type of cancer is provided. In certain aspects, an amount of BCMA or a fragment thereof in a biological sample is obtained from a subject diagnosed with the solid tumor cancer at a time point following treatment, wherein an amount of BCMA polypeptide or a fragment thereof in the biological sample of lower than about 30 ng/mL or higher than about 150 ng/mL indicates that the cancer will progress sooner. In other aspects, an amount of BCMA or a fragment thereof in a biological sample is obtained from a subject diagnosed with the solid tumor type of cancer at a time point following treatment, wherein an amount of BCMA polypeptide or a fragment thereof in the biological sample of higher than about 30 ng/mL but lower than about 150 ng/mL indicates that the cancer is more likely to enter remission or respond to treatment.

In some aspects, a method of monitoring progression or response to treatment of a solid tumor type of cancer comprises detecting an amount of BCMA or a fragment thereof in a biological sample obtained from a subject diagnosed with the cancer at a time point following treatment, wherein an amount of BCMA polypeptide or a fragment thereof in the biological sample of lower than about 30 ng/mL or higher than about 150 ng/mL indicates that the cancer will progress sooner, and wherein an amount of BCMA polypeptide or a fragment thereof in the biological sample of higher than about 30 ng/mL but lower than about 150 ng/mL indicates that the cancer is more likely to enter remission or respond to treatment, wherein the biological sample is a serum sample, or plasma sample, or supernatant obtained from a culture of the subject's bone marrow mononuclear cells or peripheral blood mononuclear cells.

In other embodiments, the diagnosis, prognosis, or monitoring of solid tumor type of cancers involves determining the relative amount of a BCMA polypeptide or a fragment thereof in a biological sample of a subject having or suspected of having a solid tumor type of cancer as compared to the amount of a BCMA polypeptide or a fragment thereof in a biological sample of a normal control subject. Thus, in certain embodiments, the diagnosis, prognosis, or monitoring of solid tumor type of cancers is monitored by the presence of at least about 2-fold, at least about 5-fold, at least about 10-fold, at least about 20-fold, at least about 50-fold, at least about 100-fold, at least about 1000-fold, or lower levels of BCMA as compared to those in a normal control subject. In general, an infective or disease state is monitored by the presence of at least about 2-fold, at least about 5-fold, at least about 10-fold, at least about 20-fold, at least about 50-fold, at least about 100-fold, at least about 1000-fold, or higher levels of BCMA as compared to those in a normal control subject. In some embodiments, lower levels of BCMA polypeptide or a fragment thereof compared to corresponding levels in healthy individuals correlate with a reduced TTP and shorter PFS. In other embodiments, lower levels of BCMA polypeptide or a fragment thereof compared to corresponding levels in healthy individuals correlate with a shortened overall survival (OS) in subjects having or suspected of having a solid tumor type of cancer. In some embodiments, the BCMA polypeptide or a fragment thereof is obtained from the subject's plasma. In other embodiments, the BCMA polypeptide or a fragment thereof is obtained from the subject's serum. Therefore, in certain embodiments, lower levels of BCMA polypeptide or a fragment thereof compared to corresponding levels in healthy individuals are predictive of a reduced PFS, reduced TTP, and/or reduced OS in subjects having or suspected of having a solid tumor type of cancer.

In some embodiments, very high levels of BCMA polypeptide or a fragment thereof compared to corresponding levels in healthy individuals also correlate with a reduced PFS, reduced TTP, and/or reduced OS in subjects having or suspected of having a solid tumor cancer. In certain embodiments, the levels of BCMA polypeptide or a fragment thereof in biological samples of subjects having or suspected of having a solid tumor cancer is higher than about 150 mg/mL.

In yet other embodiments, the diagnosis, prognosis, or monitoring of solid tumor type of cancers involves determining the relative amount of a BCMA polypeptide or a fragment thereof in a biological sample of a subject having or suspected of having a solid tumor type of cancer as compared to a predetermined cut-off value. In certain embodiments, a sample generating a signal that is statistically stronger than the predetermined cut-off value is considered positive for an infection or disease condition, whereas a sample generating a signal that is statistically weaker than the predetermined cut-off value is considered positive for an impaired immune system. In certain embodiments, the sample generates a signal that is up to about two standard deviations, up to about three standard deviations, up to about five standard deviations, up to about ten standard deviations, up to about twenty standard deviations, up to about thirty standard deviations, up to about forty standard deviations, up to about fifty standard deviations, up to about sixty standard deviations, up to about seventy standard deviations, up to about eighty standard deviations, up to about ninety standard deviations, or up to about hundred standard deviations above the predetermined cut-off. In other embodiments, the sample generates a signal that is up to about two standard deviations, up to about three standard deviations, up to about five standard deviations, up to about ten standard deviations, up to about twenty standard deviations, up to about thirty standard deviations, up to about forty standard deviations, up to about fifty standard deviations, up to about sixty standard deviations, up to about seventy standard deviations, up to about eighty standard deviations, up to about ninety standard deviations, or up to about hundred standard deviations below the predetermined cut-off.

In some embodiments, lower levels of BCMA polypeptide or a fragment thereof compared to a predetermined cut-off value correlate with a reduced TTP and shorter PFS in subjects having or suspected of having a solid tumor type of cancer. In other embodiments, lower levels of BCMA polypeptide or a fragment thereof compared to a predetermined cut-off value correlate with a shortened overall survival in subjects having or suspected of having a solid tumor type of cancer. In some embodiments, the BCMA polypeptide or a fragment thereof is obtained from the subject's plasma. In other embodiments, the BCMA polypeptide or a fragment thereof is obtained from the subject's serum. Therefore, in certain embodiments, lower levels of BCMA polypeptide or a fragment thereof compared to a predetermined cut-off value are predictive of a reduced PFS, reduced TTP, and/or reduced OS in subjects having or suspected of having a solid tumor type of cancer.

In some embodiments, very high levels of BCMA polypeptide or a fragment thereof compared to a predetermined cut-off value also correlate with a reduced PFS, reduced TTP, and/or reduced OS in subjects having or suspected of having a solid tumor type of cancer. In certain embodiments, the levels of BCMA polypeptide or a fragment thereof in biological samples of subjects having or suspected of having a solid tumor type of cancer is higher than about 150 mg/mL.

In other embodiments, the cut-off value is determined using a Receiver Operator Curve, according to the method of Sackett et al., *Clinical Epidemiology: A Basic Science for Clinical Medicine*, Little Brown and Co., 1985, p. 106-7. Briefly, in these embodiments, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for an infection or disease condition, whereas a sample generating a signal that is three standard deviations below the predetermined cut-off value is considered positive for an impaired immune system.

In some embodiments, the assay involves the use of a BCMA binding agent immobilized on a solid support to bind to and remove the BCMA polypeptide from the remainder of the sample. The bound BCMA polypeptide may then be detected using a detection reagent that contains a reporter group and specifically binds to the binding agent/polypeptide complex. Such detection reagents may comprise, for example, a binding agent that specifically binds to the BCMA polypeptide or an antibody or other agent that specifically binds to the binding agent, such as an anti-immunoglobulin, protein G5 protein A or a lectin. In some embodiments, the BCMA detection reagent, e.g., antibody, is bound to biotin which recognizes and specifically binds a streptavidin or avidin binding agent.

In certain embodiments, the assay is performed in a lateral flow or strip test format, as discussed elsewhere herein, wherein the BCMA binding agent, e.g., antibody, is immobilized on a membrane, such as nitrocellulose. In the lateral flow test, BCMA polypeptides within the sample bind to the immobilized binding agent as the sample passes through the membrane. A second, labeled binding agent then binds to the BCMA binding agent-polypeptide complex as a solution containing the second binding agent flows through the membrane. The detection of bound second binding agent may then be performed as described above. In the strip test format, one end of the membrane to which BCMA binding agent is bound is immersed in a solution containing the sample. The sample migrates along the membrane through a region containing second binding agent and to the area of immobilized binding agent. Concentration of second binding agent at the area of immobilized antibody indicates the immune status of a subject.

In particular embodiments, the method is practiced by enzyme-linked immunosorbent assay (ELISA) assay, lateral flow assay, or strip test assay using an antibody specific for BCMA.

In certain embodiments, the subjects having or suspected of having a solid tumor type of cancer are not undergoing additional therapy. In other embodiments, the subjects having or suspected of having a solid tumor type of cancer are undergoing additional therapy including, but not limited to radiation therapy, vaccine therapy, or hormone therapy. In specific embodiments, the subjects having or suspected of having a solid tumor type of cancer are additionally undergoing hormone therapy.

The invention further provides systems and kits for monitoring immune status of a subject, comprising a reagent suitable for determining levels of BCMA polypeptide or a fragment thereof in a biological sample obtained from the subject, wherein the biological sample is a serum or plasma sample or supernatant obtained from culture of the subject's bone marrow mononuclear cells or peripheral blood mononuclear cells. In some embodiments, the kit includes reagents for performing ELISA, lateral flow, or strip test assays such as an antibody specific for BCMA. Detection systems and kits of the invention are described in further detail below.

C. Detection Systems and Kits

In various embodiments, the present invention provides detection systems and kits for prognosis, diagnosis and monitoring of a solid tumor type of cancer. A detection system or kit of the present invention may be used for prognosis, diagnosis and monitoring of a solid tumor type of cancer using a biological sample, e.g., serum, of a subject. The diagnostic kit could include the method for the detection of antigen-antibody reaction in addition to the material. The detection method is preferably selected from the group consisting of flow cytometry, immunohistochemistry, and enzyme-linked immunosorbent assay (ELISA), radioimmunoassay (RIA), enzyme immunoassay (EIA), fluorescence immunoassay (FIA), luminescence immunoassay (LIA), lateral flow assay, and strip assay. The reactivity of the antigen recognition material could be confirmed using device detecting an enzyme reaction, fluorescence, luminescence, or radiation. In some embodiments, monitoring the immune status of a subject can be performed with a flow cytometry kit, immunohistochemistry kit, ELISA kit or lateral flow or strip kit including the anti-BCMA antibody or an antigen binding fragment thereof.

In some embodiments, prognosis, diagnosis, and monitoring of a solid tumor type of cancer can be performed with a flow cytometry kit, immunohistochemistry kit, ELISA kit or lateral flow or strip kit including an antibody that is specific for BCMA or a fragment thereof.

In some embodiments, a kit or system may comprise one or more or all of the following components: 1) one or more standards comprised of one or more of the biomarker(s) of the invention, such as BCMA or a fragment thereof; 2) a binding agent, such as an antibody or a plurality of antibodies, that are specific for the biomarker(s) that are to be assayed for using the kit; 3) written instructions; 4) diluents for samples and the standards; 5) a wash buffer; 6) color reagents; 7) stop solution; and 8) a carrier, such as an antibody carrier, for example, a lateral flow device, or a microplate with bound antibody, or polystyrene beads.

In other embodiments, the detection system or kit used for prognosis, diagnosis and monitoring of a solid tumor type of cancer is a quantitative ELISA that determines the concentration or concentrations of the biomarker or biomarker(s) in accordance with methods embodied by the invention. The principle of the assay is to use the quantitative sandwich enzyme immunoassay technique wherein a monoclonal or polyclonal antibody selective for a biomarker is pre-coated onto a carrier such as a microplate into its wells. The standards and sample are then pipetted into the wells and any of the biomarker that is present is bound to this immobilized antibody. Next, the wells are washed with washing buffer, and an enzyme-linked monoclonal or polyclonal antibody that is specific for the biomarker is added to the wells. Washing is again performed, and then a substrate solution is added to the wells. Color subsequently develops in proportion to the amount of polypeptide of the invention that is bound in the first step. The color development is stopped using a stop solution, and the intensity of the color is measured by a microplate reader.

In yet other embodiments, the prognosis, diagnosis and monitoring of a solid tumor type of cancer may be carried out using, for example, a lateral flow assay. Such lateral flow assays have the potential to be a cost-effective, fast, simple, and sensitive method, for instance for on-site screening assays. The lateral flow assay comprises a carrier that allows a lateral flow to occur wherein either the sample or the detection reagent is displaced form one location on the carrier to another. There are many formats of lateral flow assays suitable for use in the methods embodied by the invention, and the skilled person will readily know how to select and optimize a particular format. An example of a lateral flow test strip of the invention comprises, for example, the following components: sample pad; an absorbent pad onto which the test sample is applied; a conjugate or reagent pad that contains antibodies specific to the target analyte and conjugated to colored particles (usually colloidal gold particles, or latex microspheres); a reaction membrane, typically a hydrophobic nitrocellulose or cellulose acetate membrane onto which anti-target analyte antibodies are immobilized in a line across the membrane as a capture zone or test line (a control zone may also be present, containing antibodies specific for the conjugate antibodies); and a wick or waste reservoir, a further absorbent pad designed to draw the sample across the reaction membrane by capillary action and collect it.

There are a number of variations on lateral flow technology. The capture zone on the membrane may contain immobilized antigens or enzymes depending on the target analyte rather than antibodies. It is also possible to apply multiple capture zones to create a multiplex test. For example, in particular embodiments, test strips able to detect BCMA or a fragment thereof and separately in the same sample additional biomarkers of a specific disease, e.g., multiple myeloma, e.g., β2M, IL-6, C-reactive protein, and serum monoclonal protein are contemplated. Lateral flow immunoassays are simple to use by untrained operators and generally produce a result within 15 minutes. They are very stable and robust, have a long shelf life and do not usually require refrigeration. They are also relatively inexpensive to produce. These features make them ideal for use at the point-of-care and for testing samples in the field, as well as in the laboratory.

While most lateral flow immunoassays are only capable of providing a qualitative result, it is possible to obtain some degree of quantification by measuring the amount of conjugate bound to the capture zone. This can be done using a dedicated reader to measure the intensity of the colored test line. For example, the Neogen Corporation has developed the Accuscan™ lateral flow reader for use with its range of Reveal® assay kits and Charm Sciences also supplies a reader for its Rosa® range of test strips. More sophisticated techniques, such as fluorescent dye labeled conjugates, have also been developed to improve the quantitative potential of lateral flow assays.

A detection system in kit form can include, for example, in an amount sufficient for at least one assay a polyclonal antibody composition or a monoclonal antibody composition that binds BCMA or a fragment thereof, as a packaged reagent. Instructions for use of the packaged reagent are also typically included.

A detection system in kit form can also include, for example, a means for combining the test sample with a buffering system (Reagent 1) containing viscosity controllers and stabilizers into a reaction vessel and mixing the solution. A detection system in kit form can also include a means for reading a parameter of the reaction vessel with sample and buffer, and further means for combining the test sample and buffer mixture with a fluorescence-labeled ligand (Reagent 2) to said biological substance in the reaction vessel, mixing the solution to produce an assay solution. Furthermore, Reagent 2 may be delivered to the reaction vessel without further dilution volume of the assay solution.

As used herein, the term "package" refers to a solid matrix or material such as glass, plastic, paper, foil and the like capable of holding within fixed limits an antibody composition or monoclonal antibody composition. Thus, for example, a package can be a glass vial used to contain milligram quantities of a contemplated polypeptide or it can be a microtiter plate well to which microgram quantities of a contemplated polypeptide or antibody have been operatively affixed.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In particular embodiments, a detection system of the present invention further includes a label or indicating means capable of signaling the formation of a complex containing a polypeptide or antibody molecule of the present invention.

"Complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents such labels are themselves well-known in clinical diagnostic chemistry and constitute a part of this invention only insofar as they are utilized with otherwise novel proteins methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in *Antibody As a Tool*, Marchalonis, et al., eds., John Wiley & Sons, Ltd., pp. 189-231 (1982), which is incorporated herein by reference.

In certain embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-azino-di-(3-ethyl-benzthiazoline-G-sulfonic acid) (ABTS).

In other embodiments, the indicating group is a green fluorescent protein (GFP).

Radioactive elements are also useful labeling agents and are used illustratively herein. An exemplary radiolabeling agent is a radioactive element that produces gamma ray emissions. Elements which themselves emit gamma rays, such as $^{124}$I, $^{125}$I, $^{128}$I, $^{132}$I and $^{51}$Cr represent one class of gamma ray emission-producing radioactive element indicating groups. Particularly preferred is $^{125}$I. Another group of useful labeling means are those elements such as $^{11}$C, $^{18}$F, $^{15}$O and $^{13}$N which themselves emit positrons. The positrons so emitted produce gamma rays upon encounters with electrons present in the animal's body. Also useful is a beta emitter, such $^{111}$indium or $^{3}$H.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., *Meth. Enzymol.*, 73: 3-46 (1981). The techniques of protein conjugation or coupling through activated functional groups are particularly applicable. See, for example, Aurameas, et al., *Scand. J. Immunol.*, Vol. 8 Suppl. 7: 7-23 (1978), Rodwell et al., *Biotech.*, 3: 889-894 (1984), and U.S. Pat. No. 4,493,795, which are all incorporated herein by reference.

The detection systems or kits of the present invention can be used in an "ELISA" format to detect, for example, the presence or quantity of BCMA or a fragment thereof in a body fluid sample such as the bloodstream, plasma, serum, bone marrow, or tissue, etc. "ELISA" refers to an assay that employs an antibody or antigen bound to a solid phase and an enzyme-antigen or enzyme-antibody conjugate to detect and quantify the amount of an antigen or antibody present in a sample. Thus, for example, a polypeptide, antibody molecule composition or monoclonal antibody molecule composition of the present invention can be affixed to a solid matrix to form a solid support that comprises a package in the subject diagnostic systems. The reagent is typically affixed to the solid matrix by adsorption from an aqueous medium although other modes of affixation, well known to those skilled in the art, can be used.

Useful solid matrices are also well known in the art. Such materials are water insoluble and include cross-linked dextran; agarose; beads of polystyrene beads about 1 micron to about 5 millimeters in diameter; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any detection system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this detection assay system.

The packaging materials discussed herein in relation to detection systems are those customarily utilized in diagnostic systems. Such materials include glass and plastic (e.g., polyethylene, polypropylene and polycarbonate) bottles, vials, plastic and plastic-foil laminated envelopes and the like. In some embodiments, a detection system of the present invention is useful for assaying for the presence of BCMA or a fragment thereof. In certain embodiments, such a system comprises, in kit form, a package containing an antibody to BCMA or a fragment thereof.

All publications, patent applications, and issued patents cited in this specification are herein incorporated by reference as if each individual publication, patent application, or issued patent were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1: Serum BCMA Levels in Breast Cancer 139 breast cancer patients with metastatic hormone positive breast cancer were randomized to hormonal therapy with letrozole at two doses or megestrol acetate. Serum BCMA level in each patient was determined prior to the study treatment.

TABLE 1

Summary of BCMA Values

| Percentiles | Median | | |
|---|---|---|---|
| 1% | 11.05 | | |
| 5% | 16.84 | | |
| 10% | 25.12 | Obs | 139.00 |

TABLE 1-continued

Summary of BCMA Values

| Percentiles | Median | | |
|---|---|---|---|
| 25% | 34.20 | | |
| 50% | 55.61 | Mean | 72.44 |
| | | Std. Dev. | 104.93 |
| 75% | 78.17 | | |
| 90% | 117.80 | | |
| 95% | 164.58 | | |
| 99% | 240.31 | | |

TABLE 2

Pretreatment serum BCMA in 2$^{nd}$-line hormone therapy of metastatic breast cancer

| | | | TTP | | OS | |
|---|---|---|---|---|---|---|
| | N | % | HR | p-value | HR | p-value |
| <than | | <Cut-off | | | | |
| 15 | 6 | 4.32 | 2.60 | 0.064 | 3.81 | 0.024 |
| 20 | 10 | 7.19 | 2.88 | 0.005 | | 0.82 |
| 25 | 13 | 9.35 | 2.16 | 0.023 | | 0.22 |
| 30 | 27 | 19.42 | 1.77 | 0.016 | | 0.98 |
| 34 | | 25 | | 0.35 | | 0.98 |
| >than | | >Cut-off | | | | |
| 100 | 21 | 15 | | 0.663 | | 0.91 |
| 150 | 10 | 7.2 | | 0.46 | 0.48 | 0.039 |

TTP = time to progression; OS = overall survival.

The fact that low serum BCMA levels (<30 ng/mL groups) consistently reduced time to progression and overall survival at least in the very lowest group (<15 ng/mL) in a hormone oncology trial in hormone positive breast CA patients suggests very broad usage for serum BCMA to predict outcomes in cancer patients.

Figure 2:
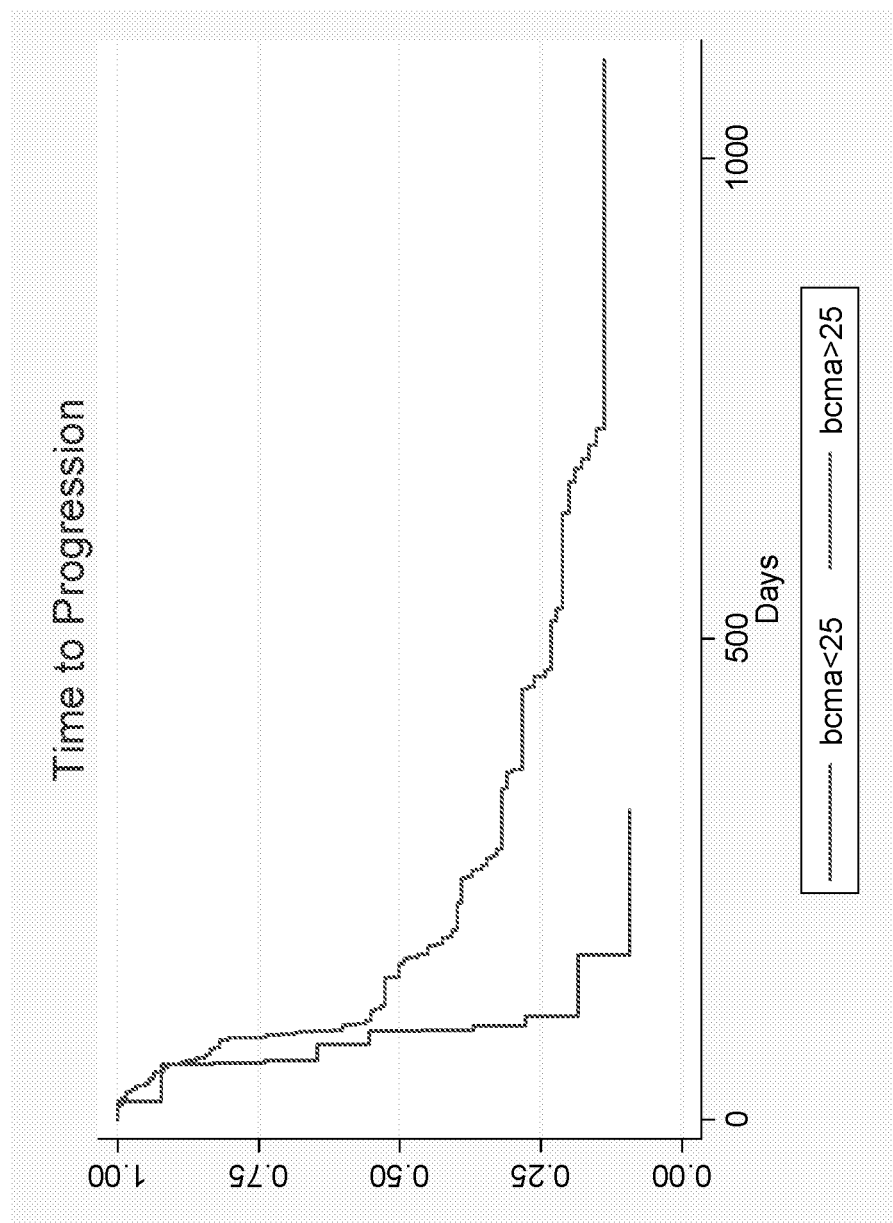
FIG. 2 shows that subjects with serum BCMA polypeptide levels lower than 25 ng/mL have reduced time to progression (TTP) of breast cancer compared to subjects with serum BCMA polypeptide levels higher than 25 ng/mL (but lower than 150 ng/mL). Therefore, serum BCMA polypeptide levels lower than 25 ng/mL correlate with reduced TTP in subjects suffering from breast cancer. Additionally, serum BCMA polypeptide levels lower than 25 ng/mL are predictive of a shorter PFS in subjects suffering from breast cancer.
Figure 3:
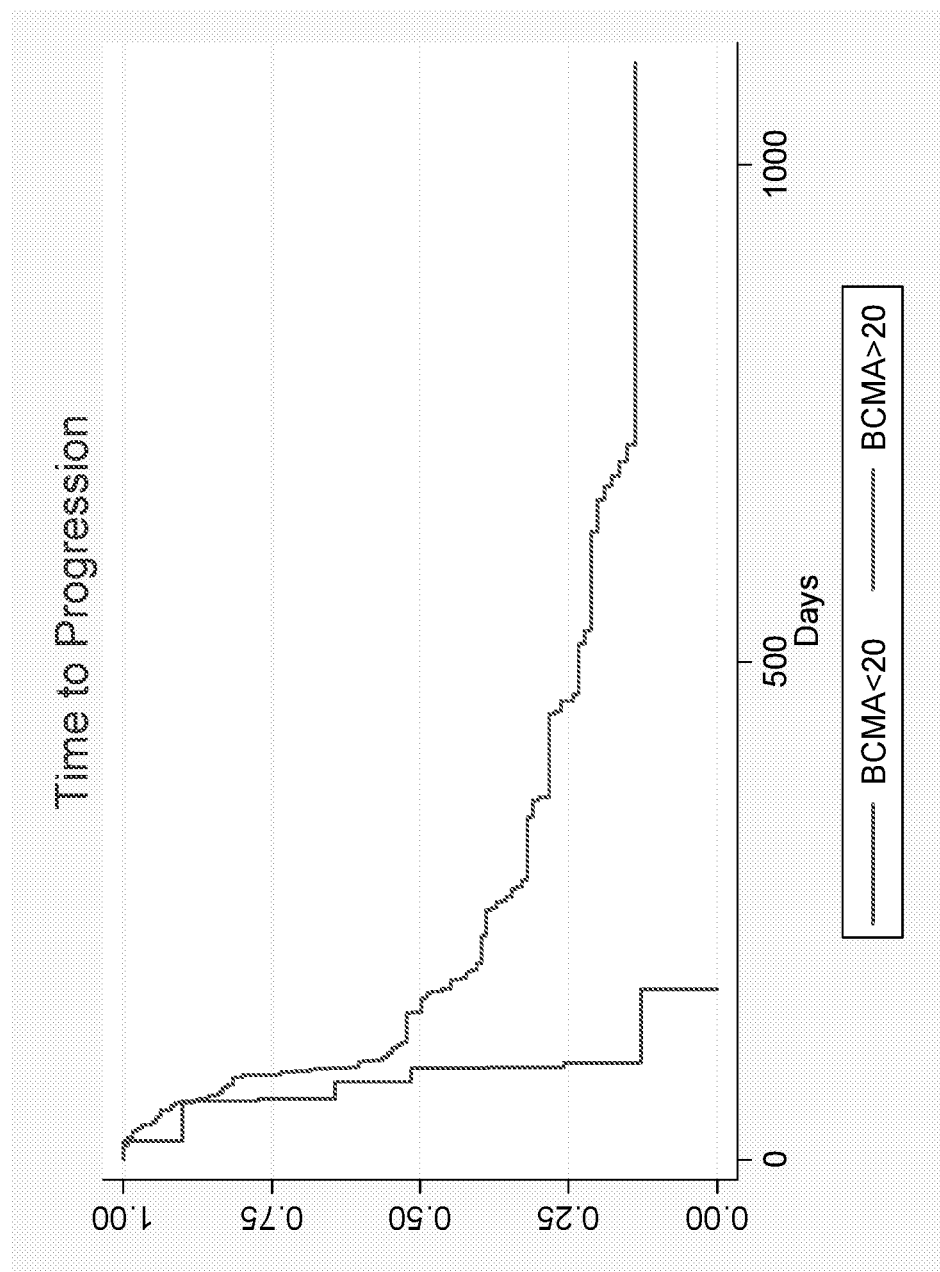
FIG. 3 shows that subjects with serum BCMA polypeptide levels lower than 20 ng/mL have reduced TTP of breast cancer compared to subjects with serum BCMA polypeptide levels higher than 20 ng/mL (but lower than 150 ng/mL). Therefore, serum BCMA polypeptide levels lower than 20 ng/mL correlate with reduced TTP in subjects suffering from breast cancer. Additionally, serum BCMA polypeptide levels lower than 20 ng/mL are predictive of a shorter PFS in subjects suffering from breast cancer.

Example 2: Serum BCMA Levels of Subjects with Breast Cancer: Serum BCMA Levels Lower Than 30 ng/mL Correlate with Reduced Time to Progression to Breast Cancer Serum from subjects with breast cancer was obtained and the serum BCMA levels were analyzed. As shown in FIG. 1, subjects with serum BCMA polypeptide levels lower than 30 ng/mL have a reduced time to progression (TTP) of breast cancer compared to subjects with serum BCMA polypeptide levels higher than 30 ng/mL (but lower than 150 ng/mL). FIG. 2 shows that subjects with serum BCMA polypeptide levels lower than 25 ng/mL have a reduced TTP of breast cancer compared to subjects with serum BCMA polypeptide levels higher than 25 ng/mL (but lower than 150 ng/mL). As expected, the TTP is further reduced compared to subjects with serum BCMA polypeptide levels lower than 30 ng/mL (FIG. 1). Additionally, FIG. 3 shows that subjects with serum BCMA polypeptide levels lower than 20 ng/mL have a reduced TTP of breast cancer compared to subjects with serum BCMA polypeptide levels higher than 20 ng/mL (but lower than 150 ng/mL). As expected, the TTP is further reduced compared to subjects with serum BCMA polypeptide levels lower than 30 ng/mL (FIG. 1) or 25 ng/mL (FIG. 2). Therefore, serum BCMA polypeptide levels lower than at least 30 ng/mL correlate with a reduced TTP in subjects suffering from breast cancer.

Figure 4:
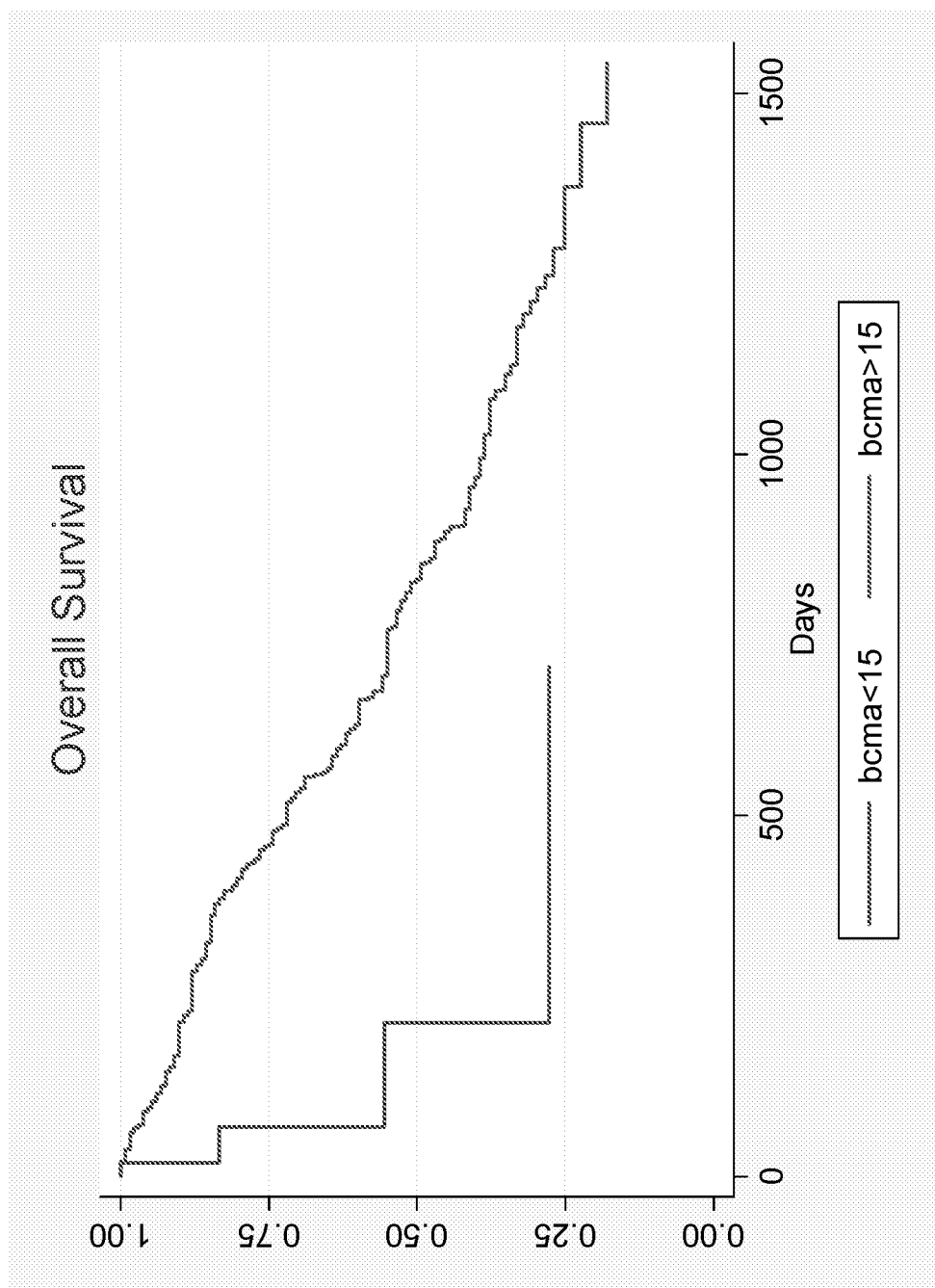
FIG. 4 shows that subjects suffering from breast cancer with serum BCMA polypeptide levels lower than 15 ng/mL have reduced OS compared to subjects with serum BCMA polypeptide levels higher than 15 ng/mL (but lower than 150 ng/mL). Therefore, serum BCMA polypeptide levels lower than 15 ng/mL correlate with reduced OS in subjects suffering from breast cancer, and are predictive of a reduced OS in such patients.

Example 3: Serum BCMA Levels of Subjects with Breast Cancer: Serum BCMA Levels Lower Than 15 ng/mL or Higher than 150 ng/mL Correlate with Reduced Overall Survival of Subjects Having Breast Cancer Serum from subjects with breast cancer was obtained and the serum BCMA levels were analyzed. As shown in FIG. 4, subjects suffering from breast cancer with serum BCMA polypeptide levels lower than 15 ng/mL have reduced overall survival (OS) compared to subjects with serum BCMA polypeptide levels higher than 15 ng/mL (but lower than 150 ng/mL). Therefore, serum BCMA polypeptide levels lower than 15 ng/mL correlate with reduced OS in subjects suffering from breast cancer, and are predictive of a reduced OS in such patients.

Figure 5:
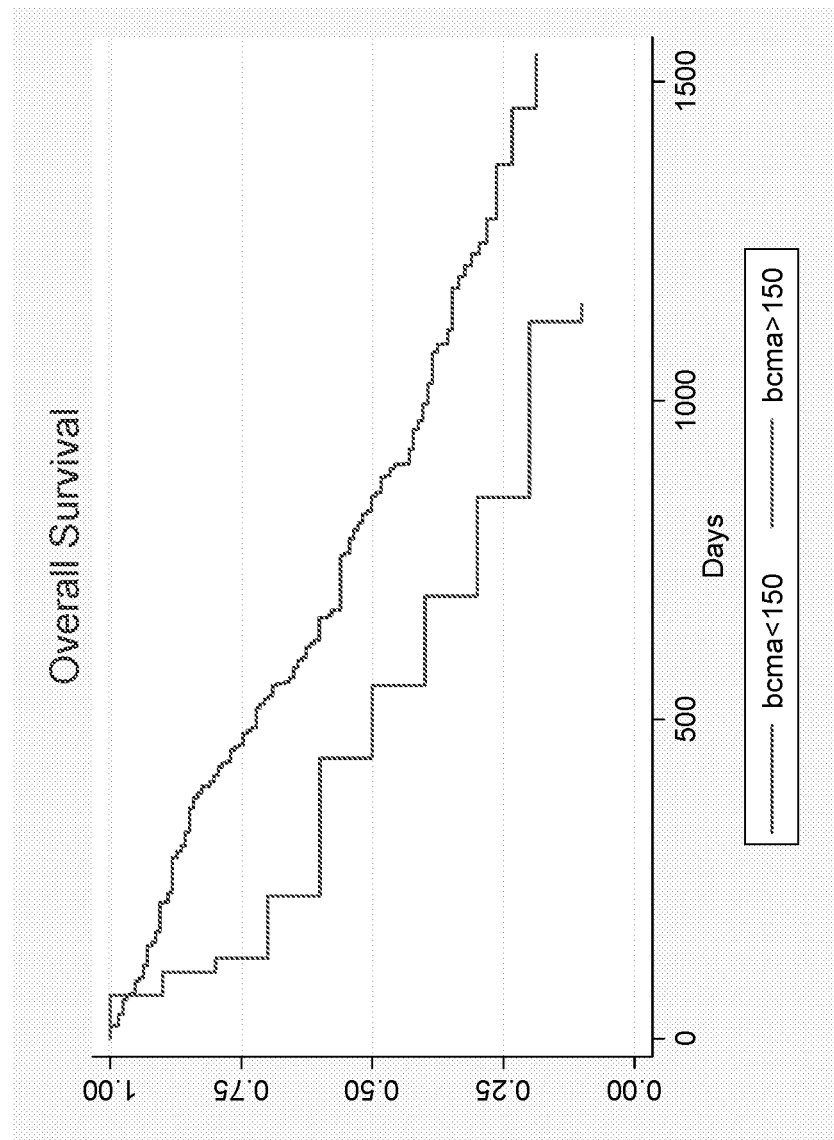
FIG. 5 shows that subjects suffering from breast cancer with serum BCMA polypeptide at very high levels (>150 ng/mL) have reduced OS compared to subjects with serum BCMA polypeptide levels lower than 150 ng/mL (but higher than 30 ng/mL). Therefore, serum BCMA polypeptide levels higher than 150 ng/mL also correlate with reduced OS in subjects suffering from breast cancer, and are predictive of a reduced OS in such patients.

Additionally, FIG. 5 shows that subjects suffering from breast cancer with serum BCMA polypeptide at very high levels (>150 ng/mL) have reduced OS compared to subjects with serum BCMA polypeptide levels lower than 150 ng/mL (but higher than 30 ng/mL). Therefore, serum BCMA polypeptide levels higher than 150 ng/mL also correlate with reduced OS in subjects suffering from breast cancer, and are predictive of a reduced OS in such patients.

Figure 6:
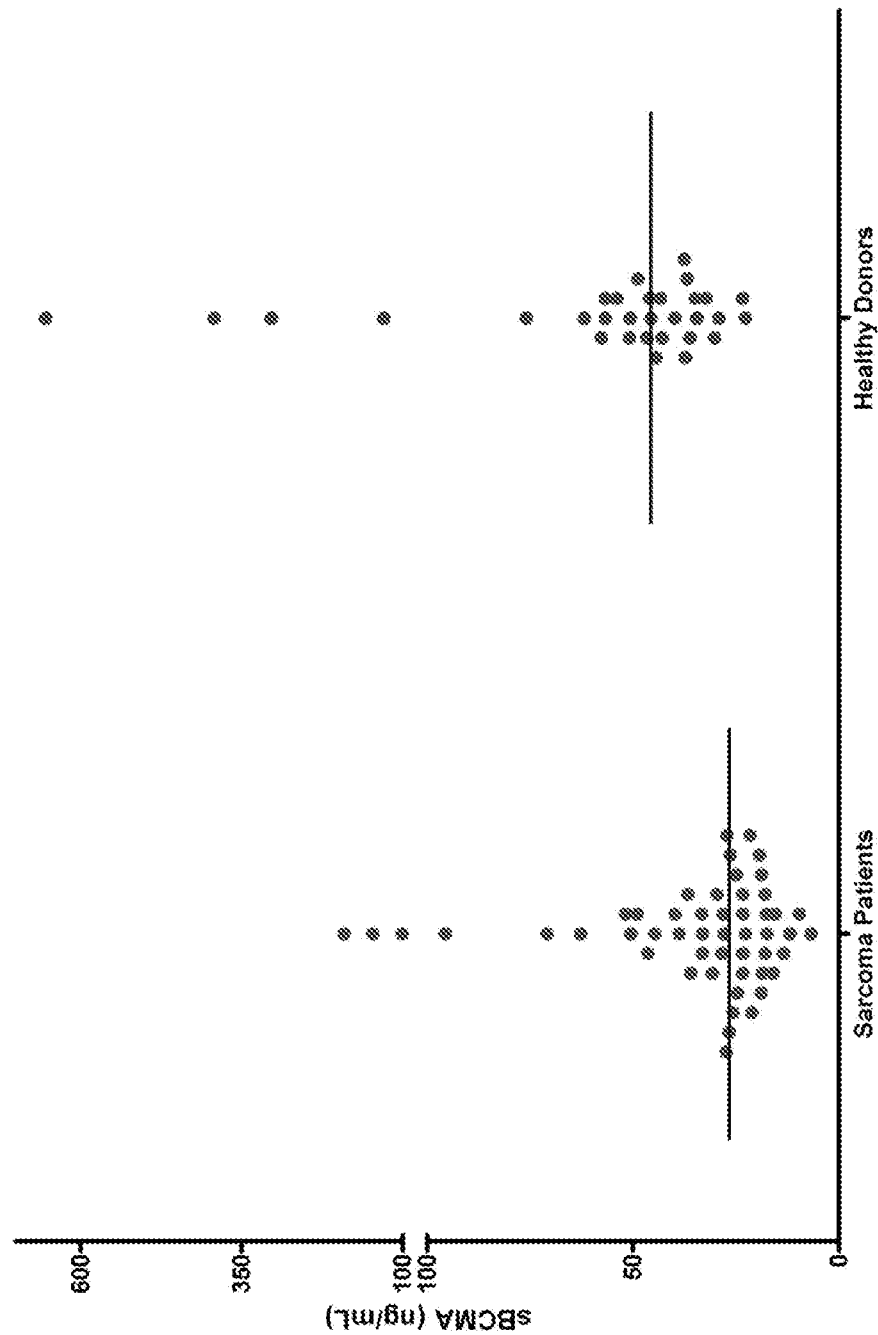
FIG. 6 shows serum BCMA levels in serum from subjects with sarcoma or healthy donors was obtained and the serum BCMA levels were analyzed. Subject suffering from sarcoma exhibited lower serum BCMA levels (p=0.0128).

Example 4: Serum BCMA Levels of Subjects with Sarcoma and Lower than Serum BCMA Levels of Healthy Donors Serum from subjects with sarcoma or healthy donors was obtained and the serum BCMA levels were analyzed. As shown in FIG. 6, subject suffering from sarcoma exhibited lower serum BCMA levels (p=0.0128). The results are summarized in Table 3.

TABLE 3

| | Sarcoma Patients | Healthy Donors |
|---|---|---|
| n = | 51 | 31 |
| Minimum | 6.806 | 22.80 |
| 25% Percentile | 18.90 | 36.26 |
| Median | 26.70 | 45.67 |
| 75% Percentile | 38.81 | 56.77 |
| Maximum | 191.1 | 654.2 |
| Mean | 36.66 | 85.76 |
| Standard Deviation | 33.18 | 131.5 |

The invention claimed is:

1. A method of treatment for a solid tumor type of cancer in a subject, comprising:
(a) detecting an amount of BCMA polypeptide or a cleaved BCMA polypeptide having at least 75% or at least 80% or at least 90% sequence identity to SEQ ID NO: 1 in a first biological sample obtained from the subject, wherein: (i) the amount of BCMA polypeptide or cleaved BCMA polypeptide in the first biological sample being lower than about 40 ng/mL correlates with a reduced time to progression (TTP) of the cancer; or (ii) the amount of BCMA polypeptide or cleaved BCMA polypeptide in the first biological sample being lower than about 40 ng/mL indicates a reduced length of progression-free survival (PFS) for the subject; or (iii) the amount of BCMA polypeptide or cleaved BCMA polypeptide in the first biological sample being lower than about 20 ng/mL or higher than about 100 ng/mL indicates a reduced overall survival (OS) for the subject;
(b) treating the subject for the solid tumor type of cancer;
(c) detecting an amount of BCMA polypeptide or a cleaved BCMA polypeptide having at least 75% or at least 80% or at least 90% sequence identity to SEQ ID NO: 1 in a second biological sample obtained from the subject at a time point following treatment wherein: (i) the amount of BCMA polypeptide or cleaved BCMA polypeptide in the second biological sample being lower than about 40 ng/mL correlates with a reduced time to progression (TTP) of the cancer; or (ii) the amount of BCMA polypeptide or cleaved BCMA polypeptide in the second biological sample being lower than about 40 ng/mL indicates a reduced length of progression-free survival (PFS) for the subject; or (iii)

the amount of BCMA polypeptide or cleaved BCMA polypeptide in the second biological sample being lower than about 20 ng/mL or higher than about 100 ng/mL indicates a reduced overall survival (OS) for the subject; and (d) comparing the amount of BCMA polypeptide or a cleaved BCMA polypeptide having at least 75% or at least 80% or at least 90% sequence identity to SEQ ID NO: 1 in the first and second samples to monitor changes in TTP, PFS or OS;

(e) Changing the treatment for the solid tumor type of cancer when the amount of BCMA polypeptide or cleaved BCMA polypeptide in the second biological sample is lower than about 40 ng/ml or higher than about 100 ng/ml; or maintaining or discontinuing treatment for the solid tumor type of cancer when the amount of BCMA polypeptide or cleaved BCMA polypeptide in the second biological sample is higher than about 40 ng/ml and lower than about 100 ng/ml.

2. The method of claim 1, (i) wherein the amount of BCMA polypeptide or cleaved BCMA polypeptide in the first biological sample being lower than about 30 ng/mL correlates with a reduced time to progression (TTP) of the cancer.

3. The method of claim 1, wherein the amount of BCMA polypeptide or cleaved BCMA polypeptide in the first biological sample being lower than about 30 ng/mL indicates a reduced length of progression-free survival (PFS) for the subject.

4. The method of claim 1, wherein the amount of BCMA polypeptide or cleaved BCMA polypeptide in the first biological sample being lower than about 15 ng/mL or higher than about 150 ng/mL indicates a reduced OS for the subject.

5. The method of claim 2, wherein the first and/or second biological sample is a serum sample.

6. A method of treatment involving monitoring progression or response to treatment of solid tumor cancer in a subject diagnosed with the cancer, comprising, (a) treating the subject for the solid tumor cancer;

(b) detecting an amount of BCMA or a cleaved BCMA polypeptide having at least 75% or at least 80% or at least 90% sequence identity to SEQ ID NO: 1 in a biological sample obtained from the subject at a time point following treatment, wherein: (i) an amount of BCMA polypeptide or cleaved BCMA polypeptide in the biological sample of lower than about 40 ng/mL or higher than about 100 ng/mL indicates that the cancer will progress sooner; or (ii) an amount of BCMA polypeptide or a fragment thereof in the biological sample of higher than about 40 ng/mL but lower than 100 ng/mL indicates that the cancer is more likely to enter remission or respond to treatment.

7. The method of claim 6, wherein an amount of BCMA polypeptide or cleaved BCMA polypeptide in the biological sample of lower than about 30 ng/mL or higher than about 150 ng/mL indicates that the cancer will progress sooner.

8. The method of claim 6, wherein an amount of BCMA polypeptide or cleaved BCMA polypeptide in the biological sample of higher than about 30 ng/mL but lower than about 150 ng/mL indicates that the cancer is more likely to enter remission or respond to treatment.

9. The method of claim 6, wherein the biological sample is a serum sample.

10. The method of claim 6, wherein the solid tumor cancer is breast cancer.

11. The method of claim 6, wherein the BCMA polypeptide or cleaved BCMA polypeptide having at least 75% or at least 80% or at least 90% sequence identity to SEQ ID NO: 1 is detected using a detection system selected from the group consisting of enzyme-linked immunosorbent assay (ELISA), radioimmunoassay (RIA), enzyme immunoassay (EIA), fluorescence immunoassay (FIA), luminescence immunoassay (LIA), lateral flow assay (LFA), and strip assay.

12. The method of claim 11, wherein the detection system is a lateral flow assay.

13. The method of claim 11, wherein the detection is performed using an antibody specific for BCMA polypeptide or cleaved BCMA polypeptide.

14. The method of claim 13, wherein the antibody specific for BCMA polypeptide or cleaved BCMA polypeptide is a monoclonal antibody.

15. The method of claim 13, wherein the antibody specific for BCMA polypeptide or cleaved BCMA polypeptide is a polyclonal antibody.

16. A method of treating breast cancer in a subject, comprising:

a) detecting an amount of BCMA polypeptide or cleaved BCMA polypeptide having at least 75% or at least 80% or at least 90% sequence identity to SEQ ID NO: 1 in a biological sample obtained from the subject; and b) if the amount is greater than 15 ng/mL, administering an effective amount of letrozole, megestrol acetate, or letrozole and megestrol acetate.

17. The method of claim 16, wherein the administering step is performed only if the amount is the amount is greater than 30 ng/mL.

18. The method of claim 16, wherein the administering step is performed only if the amount is greater than 15 ng/mL and is less than 150 ng/mL.

19. The method of claim 16, wherein the biological sample is a serum sample.

* * * * *